(12) United States Patent
Khosravi et al.

(10) Patent No.: US 6,248,546 B1
(45) Date of Patent: *Jun. 19, 2001

(54) ASSAY OF IGFBP COMPLEX

(75) Inventors: M. Javad Khosravi; Anastasia Diamandi, both of Toronto (CA); Jehangir Mistry, Leagues City, TX (US)

(73) Assignee: Diagnostic Systems Laboratories, Inc., Webster, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/036,845

(22) Filed: Mar. 9, 1998

(51) Int. Cl.[7] ............ G01N 33/543; G01N 33/545; G01N 33/577; C07K 16/22; C07K 16/28

(52) U.S. Cl. .......... 435/7.94; 435/7.5; 435/7.8; 435/7.92; 435/70.21; 435/331; 435/334; 435/335; 435/336; 435/337; 435/975; 436/518; 436/531; 436/548; 530/387.9; 530/388.22; 530/388.23; 530/388.24; 530/388.25; 530/389.2; 530/389.3; 530/391.1; 530/391.3

(58) Field of Search .................. 435/7.2, 7.5, 7.8, 435/7.92, 7.94, 70.21, 17.2, 330, 331, 334–337, 975; 436/503, 518, 531, 548, 811; 530/387.7, 387.9, 388.22–388.25, 389.2, 389.3, 391.1, 391.3; 935/104, 110

(56) References Cited

U.S. PATENT DOCUMENTS 4,271,140 * 6/1981 Bunting ................ 435/7.94

OTHER PUBLICATIONS

Rutanen et al., 1993. Measurement of insulin–like growth factor binding protein–1 in cervical/vaginal secretions: comparison with the ROM–check Membrane Immunoassay in diagnosis of ruptured fetal membranes. Clinica Chimica Acta 214: 73–81.*

OY Medix Biochemica AB, 1994. *Monoclonal Antibodies,* OY Medix Biochemica AB, Kauniainen. pp. 15–16.*

Hellstrom et al., 1985. In *Monoclonal Antibodies for Cancer Detection and Therapy* (Baldwin et al, eds.), Academic Press, London. p. 20.*

Campbell, 1991. *Monoclonal Antibody and Immunosensor Technology,* Elsevier, Amsterdam. pp. 3–6 and 45.*

Strasburger et al., 1994. Non–isotopic two–site immunoassay for IGFBP–3. Growth Regulation 4 (Suppl. 1): 138, Abstract #11348.*

Strasburger, 1994. Comparison of five commercial immunoassay kits for IGFBP–3 measurement. Growth Regulation 4 (Suppl. 1): 138, Abstract #11349.*

Tillmann, et al., "Biochemical Tests in the Diagnosis of Childhood Growth Hormone Deficiency," Journal of Clinical Endocrinology and Metabolism, vol. 82, No. 2, 1997, p. 531–535.

(List continued on next page.)

*Primary Examiner*—Christopher L. Chin
*Assistant Examiner*—James L. Grun
(74) *Attorney, Agent, or Firm*—Haynes and Boone LLP

(57) ABSTRACT

A method of assaying the growth hormone status of an individual by immuno-assay for the 150 KDa Insulin-like Growth Factor ternary complex (IGF/IGFBP-3/ALS). Alternatively, a binary complex may be assayed. The method involves capturing the IGFBP complex with a first antibody coupled to a solid phase and detecting the complex with a second antibody coupled to a label. A set of monoclonal and polyclonal antibodies usefutl for the assay is also provided.

22 Claims, 10 Drawing Sheets

1=GHRD; 2=NORMALS; 3=ACROMEGALIC; 4=GHD

OTHER PUBLICATIONS

Shimasaki, et al., "Identification and Molecular Characterization of Insulin–Like Growth Factor Binding Proteins (IGFBP–1, –2, –3, –4, –5 and –6)," Progress in Growth Factor Research, vol. 3, p. 243–266, 1991.

Rotwein, "Structure, Evolution, Expression and Regulation of Insulin–Like Growth Factors I and II," Growth Factors, 1991, vol. 5., p. 3–18.

Daughaday, et al., "Insulin–Like Growth Factors I and II, Peptide, Messenger Ribonucleic Acid and Gene Structures, Serum, and Tissue Concentrations," Endocrine Reviews, vol. 10, No. 1, 1989, p. 68–91.

LeRoith, et al, "Insulinlike Growth Factors and Their Receptors as Growth Regulators in Normal Physiology and Pathologic States," Endocrinology and Metabolism, TEM vol. 2, No. 4, Jul./Aug. 1991, p. 134–139.

Jones et al., "Insulin–Like Growth Factors and Their Binding Proteins: Biological Actions," Endocrine Reviews, vol. 16, No. 1, 1995, p. 3–34.

Rosenfeld, et al., "Insulinlike Growth Factor–Binding Proteins," Recent Progress in Hormone Research, vol. 46, p. 99–163.

Cohen, et al., "Physiologic and clinical relevance of the insulin–like growth factor binding proteins," Current Opinion in Pediatrics, vol. 6, No. 4, Aug. 1994, p. 462–467.

Baxter, et al., "Structure of the $M_r$ 140,000 growth hormone–dependent insulin–like growth factor binding protein complex: Determination by reconstitution and affinity labeling," Proc. Natl. Acad. Sci., USA, vol. 86, p. 6898–6902, Sep. 1989.

Baxter, "Characterization of the Acid–Labile Subunit of the Growth Hormone–Dependent Insulin–Like Growth Factor Binding Protein Complex," Journal of Clinical Endocrinology and Metabolism, vol. 67, No. 2, p. 265–272, 1988.

Baxter, et al., "High Molecular Weight Insulin–like Growth Factor Binding Protein Complex," The Journal of Biological Chemistry, vol. 264, No. 20, Jul. 15, 1989, p. 11843–11848.

Baxter, "Circulating Levels and Molecular Distribution of the Acid–labile ($\alpha$) Subunit of the High Molecular Weight Insulin–Like Growth Factor–Binding Protein Complex," Journal of Clinical Endocrinology and Metabolism, vol. 70, No. 5, p. 1347–1353, 1990.

Martin, et al., "Insulin–like Growth Factor Binding Protein–3: Biochemistry and Physiology," Growth Regulation (1992) 2, 88–99.

Khosravi, et al., "Acid Labile Subunit of Human Insulin–Like Growth Factor–Binding Protein Complex: Measurement, Molecular, and Clinical Evaluation," Journal of Clinical Endocrinology and Metabolism, vol. 82, No. 12, p. 3944–3951, 1997.

Giudice, "Editorial: IGF Binding Protein–3 Protease Regulation: How Sweet It Is!," Journal of Clinical Endocrinology and Metabolism, vol. 80, No. 8, p. 2279–2281, 1995.

Rajah, et al., "Insulin–Like Growth Factor Binding Protein (IGFBP) Proteases: Functional Regulators of Cell Growth," Progress in Growth Factor Research, vol. 6, Nos. 2–4, p. 273–284, 1995.

Khosravi, et al., "Immunoassay of insulin–like growth factor binding protein–1," Clinical Chemistry 43:3, p. 523–232 (1997).

Lee, et al., "Efficacy of Insulin–Like Growth Factor I Levels in Predicting the Response to Provocative Growth Hormone Testing," Pediatric Research, vol. 27, No. 1, 1990, p. 45–51, 1990.

Rosenfeld, et al., "Diagnostic Controversy: The Diagnosis of Childhood Growth Hormone Deficiency Revisited," Journal of Clinical Endocrinology and Metabolism, vol. 80, No. 5, p. 1532–1540 (1995).

Rosenfeld, "Editorial: Is Growth Hormone Deficiency a Viable Diagnosis?," Journal of Clinical Endocrinology and Metabolism, vol. 82, No. 2, p. 349–351 (1997).

Attanasio, et al., "Adult Growth Hormone (GH)–Deficient Patients Demonstrate Heterogeneity Between Childhood Onset and Adult Onset Before and During Human GH Treatment," Journal of Clinical Endocrinology and Metabolism, vol. 82, No. 1, p. 82–88 (1997).

Thoren, et al., "Serum Insulin–Like Growth Factor I (IGF–I), IGF–Binding Protein–1 and –3, and the Acid Labile Subunit as Serum Markers of Body Composition during Growth Hormone (GH) Therapy in Adults and GH Deficiency," Journal of Clinical Endocrinology and Metabolism, vol. 82, No. 1, p. 223–229 (1997).

Lee, et al., "Clinical Utility of Insulin–Like Growth Factor Assays," Disorders of Growth and Development Pediatrician 14: 154–161 (1987).

Powell, et al., "Serum Somatomedin Levels in Adults with Chronic Renal Failure: The Importance of Measuring Insulin–Like Growth Factor (IGF–I) and IGF–II in Acid–Chromatographed Uremic Serum," Journal of Clinical Endocrinology and Metabolism, vol. 63, No. 5, p. 1186–1192 (1986).

Daughaday, et al., "Inhibition of Access of Bound Somatomedin to Membrane Receptor and Immunobinding Sites: A Comparison of Radioreceptor and Radioimmunoassay of Somatomedin in Native and Acid–Ethanol–Extracted Serum," Journal of Clinical Endocrinology and Metabolism, vol. 51, No. 4, p. 781–788 (1980).

Blum, et al., "A specific radioimmunoassay for insulin–like growth factor II: the interference of IFG binding proteins can be blocked by excess IGF–I," Acta Endocrinologic (Copenh) 1988, 118:374–380.

Bang, et al., "Comparison of acid ethanol extraction and acid gel filtration prior to IGF–I and IGF–II radioimmunoassays: Improvement of determinations in acid ethanol extracts by the use of truncated IGF–I as radio ligand," Acta Endocrinological (Copenh) 1991, 124: 620–629.

Mesiano, et al., "Failure of acid–ethanol treatment to prevent interference by binding protein in radioligand assays for the insulin–like growth factors," J. Endocr. (1988) 119, 453–460.

Breier, et al, "Radioimmunoassay for insulin–like growth factor–I: solutions to some potential problems and pitfalls," Journal of Endocrinology (1991) 128, 347–357.

Mohan, et al., "Development of a Simple Valid Method for the Complete Removal of Insulin–Like Growth Factor (IGF-)–Binding Proteins for IGFs in Human Serum and Other Biological Fluids: Comparison with Acid–Ethanol Treatment and $C_{18}$ Sep–Pak Separation," Journal of Clinical Endocrinology and Metabolism, vol. 80, No. 2, p. 637–647 (1995).

Juul, et al., "Serum Insulin–Like Growth Factor–I in 1030 Healthy Children, Adolescents, and Adults: Relation to Age, Sex, Stage of Puberty, Testicular Size, and Body Mass Index," Journal of Clinical Endocrinology and Metabolism, vol. 78, No. 3, p. 744–752 (1994).

Juul, et al., Serum Levels of Insulin–Like Growth Factor (IGF)–Binding Protein–3 (IGFBP–3) in Healthy Infants, Children, and Adolescents: The Relation to IGF–I, IGF–II, and IGFBP–1, IGFBP–2, Age, Sex, Body Mass Index, and Pubertal Maturation, Journal of Clinical Endocrinology and Metabolism, vol. 80, No. 8, p. 2534–2542 (1995).

deBoer, et al., "Monitoring of Growth Hormone Replacement Therapy in Adults, Based on Measurement of Serum Markers," Journal of Clinical Endocrinology and Metabolism, vol. 81, No. 4, p. 1371–1377 (1996).

Khosravi, et al, "Noncompetitive ELISA for human serum insulin–like growth factor–I," Clinical Chemistry 42:8 p. 1147–1154 (1996).

Khosravi, et al., "Novel Application of Streptavidin–Hapten Derivatives as Protein–Tracer Conjugate in Competitive–Type Immunoassays Involving Biotinylated Detection Probes," Clinical Chemistry, vol. 37, No. 1, p. 58–53 (1991).

Khosravi, et al., "An ultrasensitive Immunoassay for Prostate–Specific Antigen Based on Conventional Colorimetric Detection," Clinical Biochemistry, vol. 28, No. 4, p. 407–414, 1995.

Khosravi, et al., "Immunofluorometry of Choriogonadotropin by Time–Resolved Fluorescence Spectroscopy, with a New Europium Chelate as Label," Clinical Chemistry, vol. 33, No. 11, p. 1994–1999 (1987).

Vorwerk, et al., "Synthesis of IGFBP–3 Fragments in a Baculovirus System and Characterization of Monoclonal Anti–IGFBP–3 Antibodies," Journal of Clinical Endocrinology and Metabolism, vol. 82, No. 7, p. 2368–2370 (1997).

Booth et al., "IGFBP–3 proteolysis by plasmin, thrombin, serum: heparin binding, IGF binding, and structure of fragments," Am. J. Physiol. 271:E465–E470 (1996).

Manes, et al., "Functional Epitope Mapping of Insulin–Like Growth Factor I (IGF–I) by anti–IGF–I Monoclonal Antibodies," Endocrinology, vol. 138, No. 3, p. 905–915 (1997).

Barreca, et al. "Effect of the Acid–labile Subunit on the Binding of Insulin–Like Growth Factor (IGF)–Binding Protein–3 to [$^{125}$I]IGF–I," Journal of Clinical Endocrinology and Metabolism, vol. 80, No. 4, p. 1318–1324 (1995).

Hasegawa, et al., "High Ratios of Free to Total Insulin–Like Growth Factor–I in Early Infancy," Journal of Clinical Endocrinology and Metabolism, vol. 82, No. 1, p. 156–158 (1997).

Liu, "Immunoblot Studies of the IGF–Related Acid–Labile Subunit," Journal of Endocrinology and Metabolism, vol. 79, No. 6, p. 1883–1886 (1994).

* cited by examiner

1=GHRD; 2=NORMALS; 3=ACROMEGALIC; 4=GHD

ASSAY OF IGFBP COMPLEX

BACKGROUND OF THE INVENTION

1. Field of the Invention

This invention relates to methods of determining the growth hormone status of an individual. This is performed by measuring the circulating Insulin-like Growth Factor binary or ternary complex (150 KDa complex containing IGF, IGFBP and ALS). The complex is first captured with a monoclonal antibody that is coupled to a solid support and called a "capture-antibody" herein. One of the members of the complex is detected with a monoclonal antibody called a "detection-antibody" herein.

Ideally, the capture- and detection-antibodies do not interfere with each other or with complex formation. For this reason, we have prepared a series of monoclonal antibodies and mapped their epitopes. The invention also pertains to said monoclonal antibodies and kits containing the same.

2. Background

The super family of insulin-like growth factors (IGFs) includes IGF-I and -II, at least six high affinity IGF binding proteins (IGFBP-1 to IGFBP-6), an acid-labile protein subunit (ALS), and various cell surface receptors, proteases and antagonists. The IGF superfamily is intimately involved in the regulation of cellular growth and metabolism (1–4). IGFs are produced by multiple normal and malignant tissues and are present in blood and other biological fluids in close association with IGFBPs which specifically bind and modulate their bioactivities (4–9). IGF-I, a 7.5 KDa peptide, is the major mediator of the in vivo mitogenic and metabolic effects of growth hormone (GH) and, as with IGF-II, its actions are mediated by both endocrine and autocrine-paracrine mechanisms (1–4).

Most of the IGF circulates with an approximately 150 KDa ternary protein complex consisting of IGFBP-3 and ALS (4–9). Binding of ALS to IGFBP-3 depends on IGFBP-3 occupancy by IGF-I or IGF-II and under normal conditions, nearly all of the circulating IGFs (>95%) are found in the ternary complex (4–12). IGFBP-3 is normally the major carrier of IGF in serum and its association appears to stabilize daily IGF levels (half-life of ~12–15 hrs) and limit IGF access to extracellular compartments (4–9). It is presumed that most IGFs are found in the ternary complex because ALS is present at significantly higher molar excess than IGFBP-3 or the IGF peptides (13, 14). Smaller proportions of circulating IGFs are associated with other IGF binding proteins and less than 1% has been estimated to exists in an unbound or "free" form.

While the precise biological relevance of the ternary complex has not been clearly defined, circulating levels of its constituents, and thus formation of the ternary complex, is highly GH-dependent (4–9). Serum IGF-I, IGFBP-3 and ALS are low in GH deficiency and are elevated in acromegalic subjects (4–9, 13, 15). Post-translational modifications of IGFBPs, including proteolysis (16, 17) and phosphorylation (18, 19), are apparently involved in modulating bioavailability of the IGF peptides.

The clinical assessment of GH status has been controversial, primarily due to the episodic nature of GH secretion, its relatively short circulating half-life and considerable variability in GH measurement by different methods (20, 21). Currently, clinical evaluation of GH sufficiency may involve multiple venous blood sampling for determination of GH secretion in response to a number of physiological or pharmacological stimuli. Because of the reported limitations of provocative GH testing, which include arbitrary definition of diagnostic cut-off levels, and potential health risk and cost, alternative screening procedures have been sought (20, 21).

As blood IGF-I, IGFBP-3 and ALS levels are highly dependent on GH secretion (4–9, 13, 15), appropriate determination of their serum levels have been endorsed as the most effective means in the evaluation of GH-IGF axis status, particularly in children with short stature (21–23). Determinations of IGF-I and ALS may be also valuable in the diagnosis of adult GH deficiency and monitoring of therapeutic response to GH replacement therapy (24, 25).

The high levels of association with IGFBPs has been a major concern in routine immunoassay of serum IGF-I because IGFBPs may mask reactive epitopes or compete with antibodies for tracer binding. Reliable determination of IGF-I in serum requires dissociation and removal of IGFBPs before analysis (26). Present strategies are based on serum acidification to irreversibly denature ALS and disrupt the ternary complex, followed by procedures to remove most or all of the IGFBPs. Size exclusion chromatography in acid is considered the "gold standard" method for the latter step (27), but is not practical for efficient high-volume sample processing.

The most commonly used alternative is acid-ethanol precipitation (28). However, the method may leave substantial residual amounts of IGFBPs (19, 29–32). We recently confirmed that IGFBPs, in particular low molecular weight IGFBPs such as IGFBP-1, may be retained in significant quantities after acid-ethanol precipitation (19). The residual amounts of IGFBPs could compete with the detection-antibody, particularly in competitive RIAs (29) where the amount of antibody and labelled IGF-I is small relative to the concentration of analyte and residual IGFBPs. This phenomenon may account for the well known propensity of IGF-I RIAs to give false estimates of IGF-I levels in samples with high levels of endogenous IGFBPs (27, 29, 30, 32).

Various means have been devised to minimize the interference of residual IGFBPs, including addition of IGF-II to the assay mixture, acid-ethanol cryoprecipitation, use of analog tracers with low affinity for IGFs or acid-Bio-Spin chromatography (29, 30, 32, 33). However, these methods further add to the complexity of the assay and may not completely resolve the IGFBP-interference problem.

The clinical assessment of IGF-I, IGFBP-3 and ALS is further complicated by the differential effects of age, pubertal stage of development and nutritional factors on their circulating levels (21, 34, 35). Accordingly, current recommendations suggest use of IGF-I, IGFBP-3 and ALS in younger age group, and IGF-I and ALS in adult subjects (21–26, 36). As nearly all of serum IGF-I, IGFBP-3 (4–12) and as much as 50% of ALS (13, 15) are present in the high molecular weight IGFBP-3 ternary protein complex, direct determination of the complex may represent an ideal and potentially superior screening alternative. However, until now, no one has presented a reliable, accurate and simple means of quantifying the level of IGFBP complex.

SUMMARY OF THE INVENTION

ABBREVIATIONS AND DEFINITIONS

ALS—Acid Labile Subunit—A protein found in the 150 KDa ternary complex where most of the circulating IGF is found. ALS is sensitive to inactivation by acid.

Antibodies—The antibodies described herein include ten mouse monoclonal antibodies against recombinant human IGFBP-3 called B1 to B10; a polyclonal antibody against recombinant human IGFBP-3 called pB11, two mouse monoclonal antibodies to the C and N terminals of recombinant human IGF-I called I-1 and I-2, respectively; a polyclonal antibody to recombinant human IGF-II called pI-3, and two polyclonal antibodies to N and C terminal peptide fragments of human ALS called pA-1 and pA-2, respectively. Additional antibodies may be generated by methods well known in the art and evaluated as described herein.

Binary complex—A two part complex of IGFBP and ALS or of IGFBP and IGF.

Body fluid—Any biological fluid, including but not limited to the following: serum, plasma, lymph fluid, synovial fluid, follicular fluid, seminal fluid, amniotic fluid, milk, mammary fluid, whole blood, urine, spinal fluid, saliva, sputum, tears, perspiration, mucus tissue culture medium, tissue extracts and cellular extracts.

BSA—Bovine serum albumin.

Capture-antibody—An antibody that can be used to capture the IGFBP complex.

Capture-antibody coupled to a solid support—The coupling of the antibody to the solid support may be any of the well known coupling means, including covalent, non-covalent, magnetic means and the like. Commonly used cross-linking agents for attaching the capture-antibody to the solid phase substrate include, for example, 1,1-bis(diazoacetyl)-2-phenylethane, glutaraldehyde, N-hydroxysuccinimide esters, homobifunctional imidoesters, and bifunctional maleimides. Derivatizing agents, such as methyl-3-[(p-azidophenyl) dithio] propioimidate, yield photoactivatable intermediates capable of forming cross-links in the presence of light. The coupling of antibodies to various solid supports is well known in the art and need not be detailed herein.

Control standard—A sample of IGFBP complex of known concentration.

Detection-antibody—An antibody that can be detected in some manner.

Detection-antibody coupled to a label—A detection-antibody labelled by any means. The detection-antibody may be inherently labelled, for example by an incorporated radioisotope or modified amino acid or by its species specific antigenic determinants. Additionally, the antibody may be labelled by means of a detectable moiety (label) coupled to the antibody.

ELISA 1—An ELISA based on the capture of IGFBP complex with anti-IGFBP B3 and detection with anti-IGF-II-1.

ELISA 2—An ELISA based on the capture of IGFBP complex with anti-IGFBP B2 and detection with anti-IGF-I pA-1.

GH—Growth hormone.

GHRD—Growth hormone receptor defective.

GHD—Growth hormone deficiency.

GH status—The growth hormone status of an individual is reflected in the levels of GH, IGF, IGFBP, IGFBP complex or ALS as well as by other molecules related to the GH and IGF cascades. The GH status of an individual is known to vary -either up or down—in certain growth-related disease states, such as hypoglycaemia, diabetes, deficient nutritional states, certain cancers such as breast cancer and prostate cancer, immune deficiencies, fetal growth retardation, gigantism, acromegaly, hyperpituitarism, pituitary dwarfism, GH deficiency, GH excess, GH receptor defect, thyomegalia and certain CNS diseases such as Alzheimer. Therefore, many diseased individuals (human or animal) could benefit from the monitoring of growth hormone status. Additionally, there are other applications such as the monitoring of nutritional status, reproductive health, performance of racing and other performance individuals, improved breeding stock, and the like.

HRP—Horse radish peroxidase.

IGF—Insulin-like Growth Factor.

IGFBP—An IGF binding protein, including IGFBP-1 to 6 and the heretofore unsequenced IGFBPs. Preferably, the IGFBP is IGFBP-3 in the context of the assay described herein.

IGFBP-3—The major circulating IGF binding protein.

IGFBP complex—This term is defined herein to include either the binary complex of IGFBP and ALS or IGF or the ternary complex of IGFBP and ALS and IGF.

Label—Any detectable marker or detectable functionality that does not interfere with the binding of the antibody to its epitope, including but not limited to, a radioisotope, an enzyme, a fluorescent label or other measurable tag as described in U.S. Pat. No. 4,275,149 and U.S. Pat. No. 4,318,980. Numerous labels are known for use in immunoassay, including those that may be detected directly, such as fluorochrome, chemiluminescent and radioactive labels, as well as moieties, such as enzymes, that must be reacted or derivatized to be detected. Examples of labels include the radioisotopes $^{32}P$, $^{14}C$, $^{125}I$, $^{3}H$, and $^{131}I$, fluorophores such as rare earth metals or fluorescein and its derivatives, rhodamine and its derivatives, dansyl, umbelliferone, luceriferases, luciferin, green fluorescent protein, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as horse radish peroxidase, lactoperoxidase, or microperoxidase, biotin/avidin, spin labels, bacteriophage labels, stable free radicals, and the like. Additionally, the antibody itself may inherently comprise a label, for example where the detection means involves a second antibody directed against antibodies from the species from which the antibody was obtained. The preferred label is horse radish peroxidase or biotin. The number and types of labels are numerous and need not be fully described here.

PSA—Prostate specific antigen.

RT—Room Temperature.

SD—Standard deviation.

Solid support—A solid phase used for immobilization of the capture-antibody which may be any inert support or carrier that is essentially water insoluble and useful in immunoassays, including supports in the form of surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like, including 96-well micro-titre plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537 and 4,330,440 are suitably employed for capture-antibody immobilization. The preferred solid phase used herein is a multi-well micro-titre plate that can be used to analyze several samples at one time. The number and types of solid supports are numerous and need not be fully described here.

Ternary complex—The 150 KDa complex composed of IGF, IGFBP and ALS.

Treatment designed to influence growth hormone status—Includes any medical treatment whose intended effect is to influence the GH or IGF cascades. Treatments may include treatments with such agents as GH, GHBP, IGF, IGFBP, ALS, IGFBP complex, GH receptors, IGF receptors, antibodies or inhibitors of any of the preceding, receptor antagonists for GH or IGF, or any drug that acts to modulate the growth hormone status of an individual, including tamoxifen, somatostatin, somatostatin analogues, GH antagonists, IGF antagonist, IGFBP stimulators, retinoids, TGF-beta, and vitamin D analogues, and the like. Individuals include both human and animals, such as pigs, cattle, sheep, goats, horses, poultry, cats, dogs, fish, etc.

We have recently described non-competitive ELISAs for the determination of IGF-I (37), IGF-II (38), IGFBP-1 (19), IGFBP-3 (39) and ALS (15) in serum and other physiological fluids. Clinical assessment of GH-related disorders and monitoring of GH therapeutic regimes increasingly involve biochemical determinations of circulating IGF-I, IGFBP-3 and ALS levels (21–26, 36). As nearly all of blood IGF-I and IGFBP-3 (4–12) and as much as 50 percent of ALS (13, 15) are normally confined within the GH-dependent 150 KD ternary complex, direct determination of the complex may have significant advantages. We hereby report the development of highly specific and rapid ELISAs for the direct measurement of the high molecular weight IGF-binding protein complexes.

Generally speaking, the method for quantitative measurement of IGFBP complex involves capture of the complex with a first capture-antibody, washing away all unbound components, and detecting the remaining complex with a second detection-antibody. The possible immunoassay designs are based on numerous "capture and detection-antibody" combinations, and may involve combinations of (a) anti-IGFBP-3 antibodies, (b) anti-IGF-I antibodies, (c) anti-ALS antibodies, and (d) anti-complex antibodies, provided that each antibody pair (or triplet) reacts with separate epitopes and does not interfere with complex formation.

More specifically, we have exemplified the invention with an anti-IGFBP-3 capture-antibody and detection by an antibody directed against either ALS or IGF. Our approach eliminates the need for complex sample pre-treatment procedures, allows combined determination of the IGFBP complex components in a single assay, and potentially provides better clinical information.

Depending on the assay design, the ternary as well as any binary complex may be quantified, while contributions by fragments and less tightly bound or dissociable variants are eliminated.

Two specific capture-detection-antibody pairs are exemplified below and called ELISA-1 and ELISA-2. ELISA-1 involves an IGFBP-3/IGF-I antibody combination and is specific for both IGFBP-3/IGF-I/ALS ternary complexes and any binary IGFBP-3/IGF-I complex that could be potentially present. The specificity of the assay for such binary complexes was established by analysing samples before and after acid-neutralization, which is known to functionally inactivate ALS. ELISA-1 measured similar IGFBP-3 complex levels in untreated and acid-treated samples.

ELISA-2 involves an IGFBP-3/ALS antibody combination and quantifies both IGF-I as well as IGF-II-based ternary complexes and binary IGFBP-3/ALS complex. As expected, ELISA-2 did not detect any immuno-reactivity in acid-treated samples.

It is also possible to modify the assay to detect other entities. For example, it is possible to detect total IGFBP (complexed and free) with a variation of the ELISA 1 and 2. First, all IGFBP is captured with an anti-IGFBP antibody. Next, the captured IGFBP is saturated with exogenous ligand (either IGF and/or ALS depending on which detection-antibody is employed) before detection with the detection-antibody. In this assay design, both complexed IGFBP and free IGFBP will be captured by the capture-anbody, driven to complete association with the exogenous ligand, and detected by the anti-IGF or anti-ALS detection-antibody.

Further, although we have exemplified assays wherein the capture-antibody is an anti-IGFBP antibody, it is also possible to use anti-IGF, anti-ALS or an anti-complex antibody as the capture-antibody. It is apparent that various assay designs may be optimized by one of skill in the art as described herein.

The invention includes a kit for the assay of an IGFBP-complex. The kit contains a capture-antibody and a detection-antibody, provided that the capture- and detection-antibodies do not bind to overlapping epitopes and do not interfere with said IGFBP complex formation. The capture-antibody may be bound to a solid support and the detection-antibody is generally labelled in some manner.

The capture- and detection-antibody combinations may be selected from the group consisting of B1, B2, B3, B4, B5, B6, B7, B8, B9, B10, pB11, I-1, I2, pI-3, pA-1 and pA2. However, preferably, the antibody pair is B3 and I-1. In an additional preferred embodiment, the antibody pair is B2 and pA-1.

The kit may contain other useful reagents, such as a label detection means, a binding buffer, a wash buffer, a detection buffer and a control standard, and the like.

The invention also embodies a method of detecting IGFBP complex in a body fluid. The method consists of a) contacting a solid phase coupled to a capture-antibody with a body fluid to capture an IGFBP complex; b) washing the solid phase with a first wash buffer; c) contacting the solid phase with a detection-antibody coupled to a label; d) washing the solid phase with a second wash buffer; and e) detecting said label remaining with said solid phase after said washing step.

This method can advantageously be employed to determine the GH status of an individual, including, but not limited to human, bovine, porcine, equine, canine, feline, or ovine individuals. Other specific applications include, but are not limited to: a) monitoring the effect of treatments designed to influence the GH or IGF status of an individual; b) monitoring the clinical status and/or treatment of individuals with various diseases affected by GH status, including hypoglycaemia, diabetes, deficient nutritional states, certain cancers such as breast cancer and prostate cancer, immune deficiencies, fetal growth retardation, gigantism, acromegaly, hyperpituitarism, pituitary dwarfism, GH deficiency, GH excess, GH receptor defect, thyomegalia and certain CNS diseases such as, but not limited toAlzheimers; c) determining an individual's susceptibility for growth-related disease states, where susceptibility is characterized by aberrant or elevated GH status; or d) various veterinary applications such as monitoring of nutritional status, reproductive health, performance of racing and other performance indices, detecting improved breeding stock, disease resistance, and the like.

Four antigenic regions were defined. Overlapping circles indicate no sandwich formation, touching circles indicate interfering sandwich formation, and separate circles indicate independent epitopes.

Figure 2:
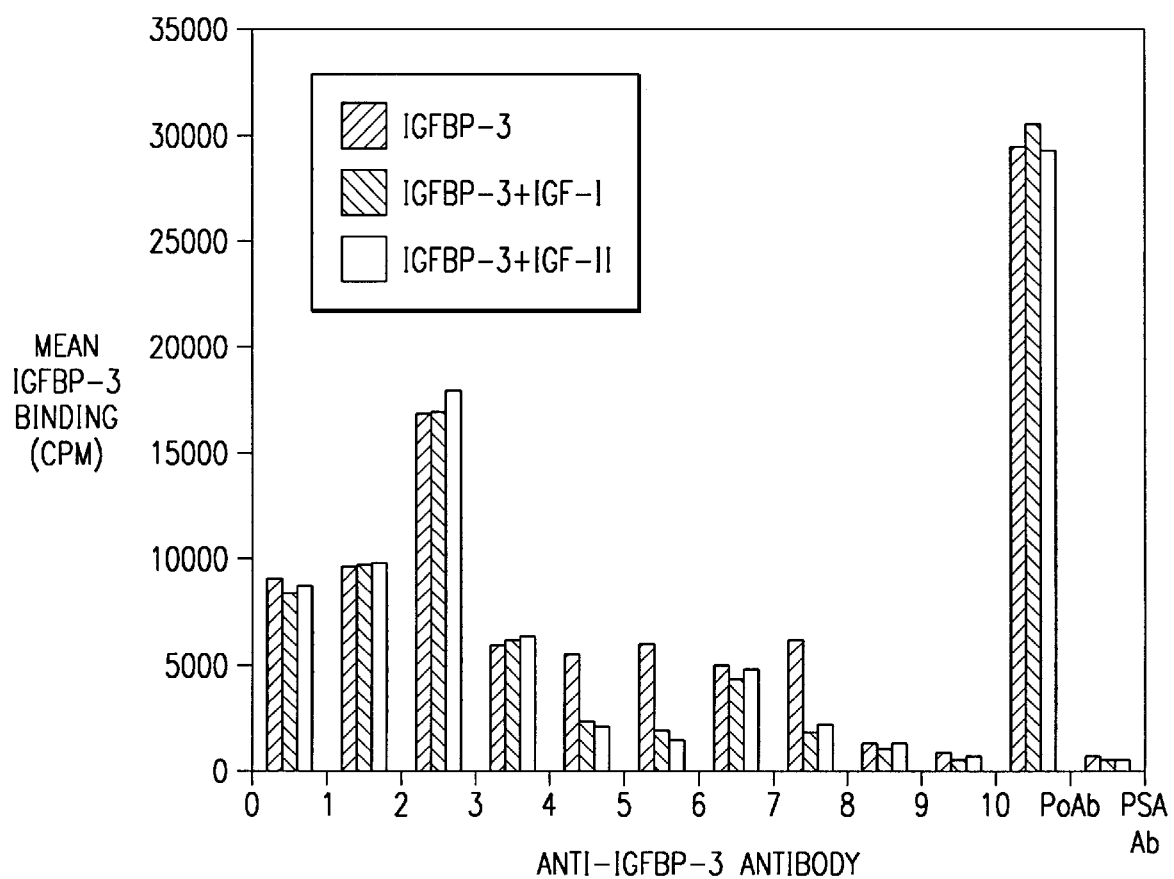

FIG. 2. Inhibition of Antibody Binding to IGFBP-3 by IGF-I and IGF-II.

Binding of anti-IGFBP-3 monoclonal and polyclonal antibodies to IGFBP-3 before and after pre-incubation with $^{125}$-IGF-I or $^{125}$-IGF-II are shown. Anti-PSA antibody was used as a negative control. Values are the mean of three measurements.

Figure 3A:
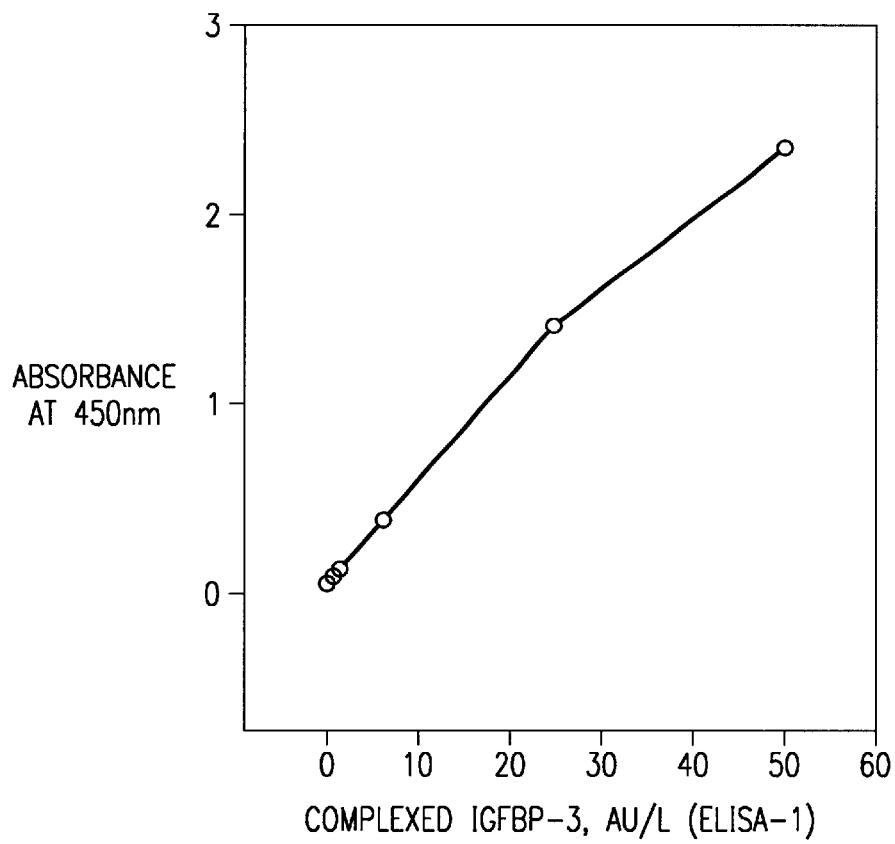
Figure 3B:
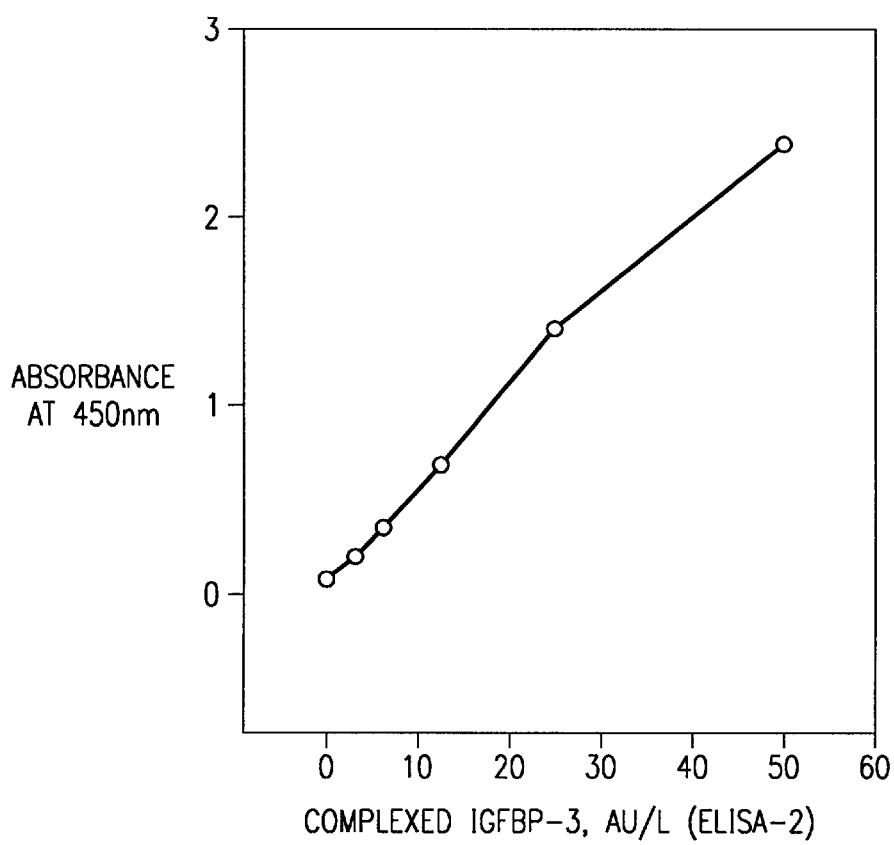

FIGS. 3A–3B. IGFBP-3 Complex ELISA Calibration Curve.

Linear-linear plots of typical ELISA-1 (FIG. 3A) and ELISA-2 (FIG. 3B) calibration curves are shown.

Figure 4A:
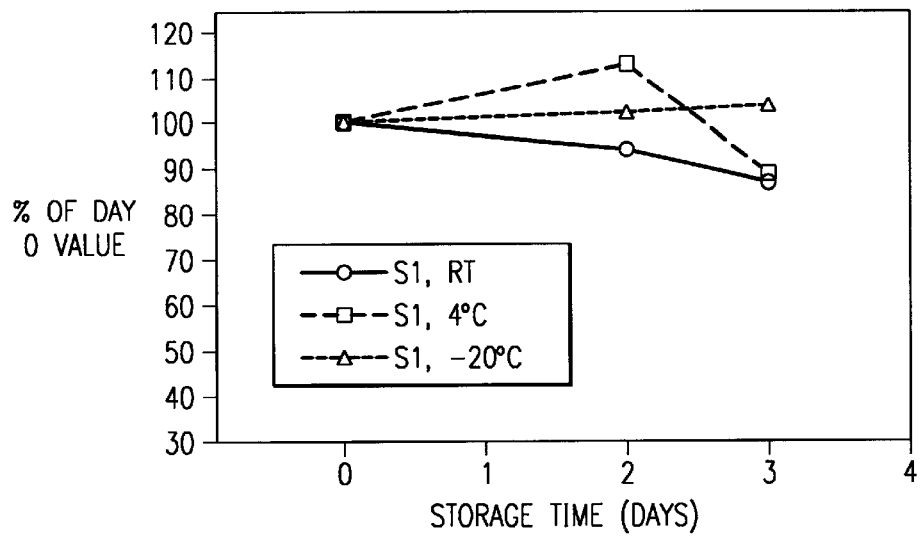
Figure 4B:
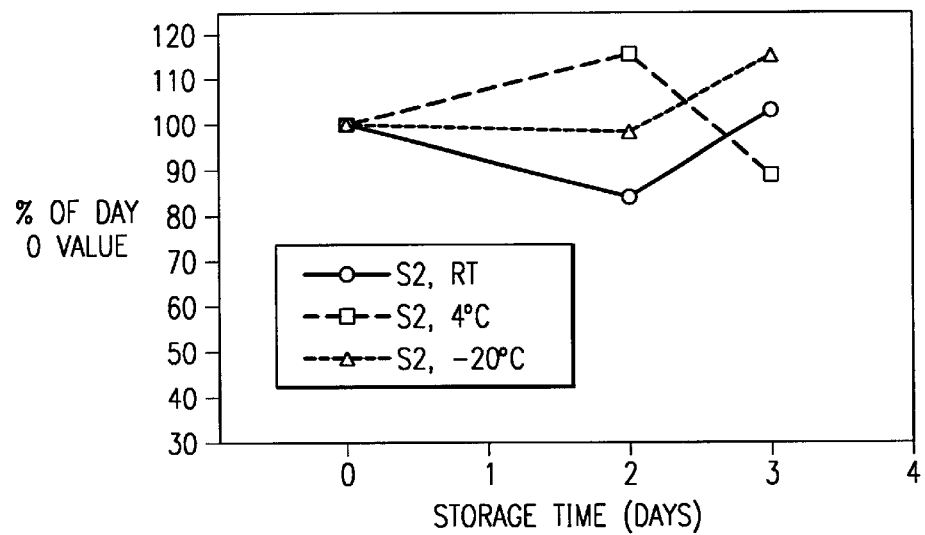
Figure 4C:
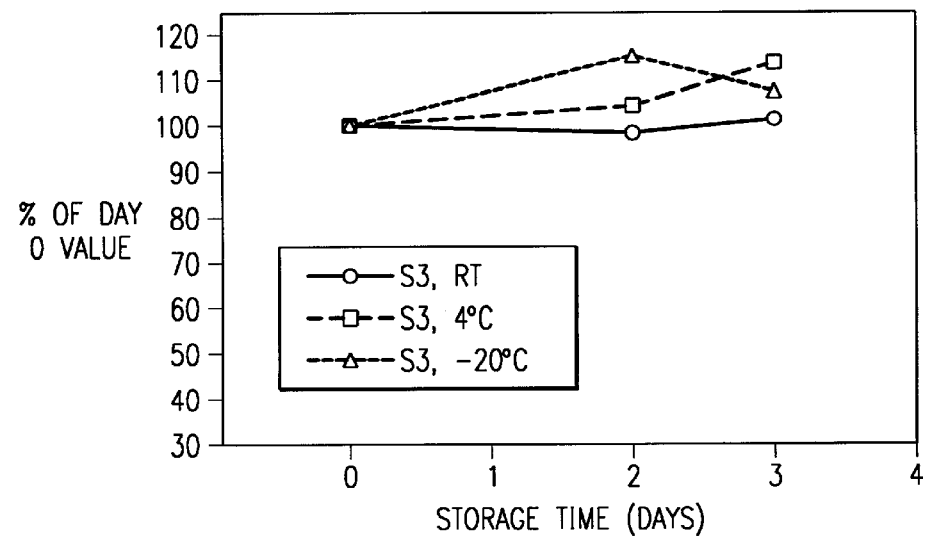

FIGS. 4A–4C. Stability of IGFBP-3 Complex Analysed by ELISA-1.

Replicate aliquots of three different samples (S1=FIG. 4A, S2=FIG. 4B, S3=FIG. 4C) stored at various temperature and analysed as indicated. Percent changes from the day 0 value are shown.

Figure 5A:
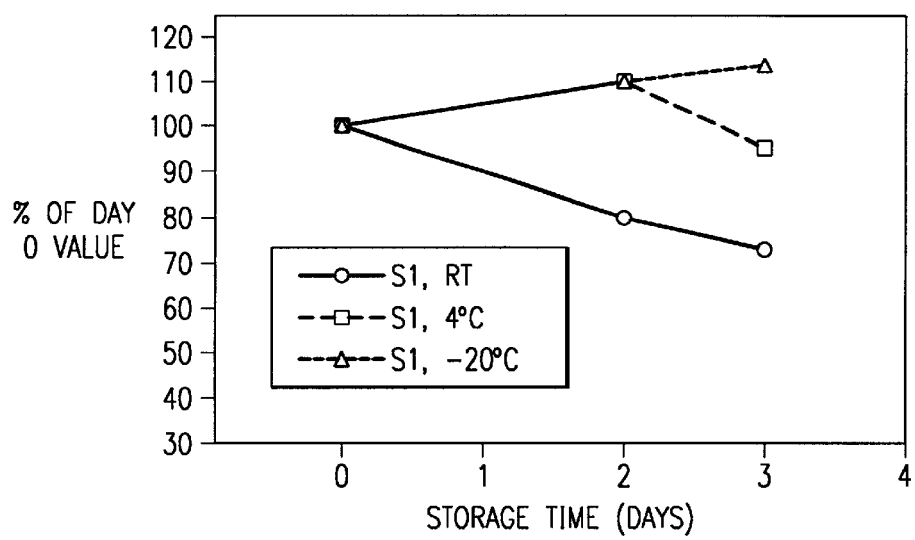
Figure 5B:
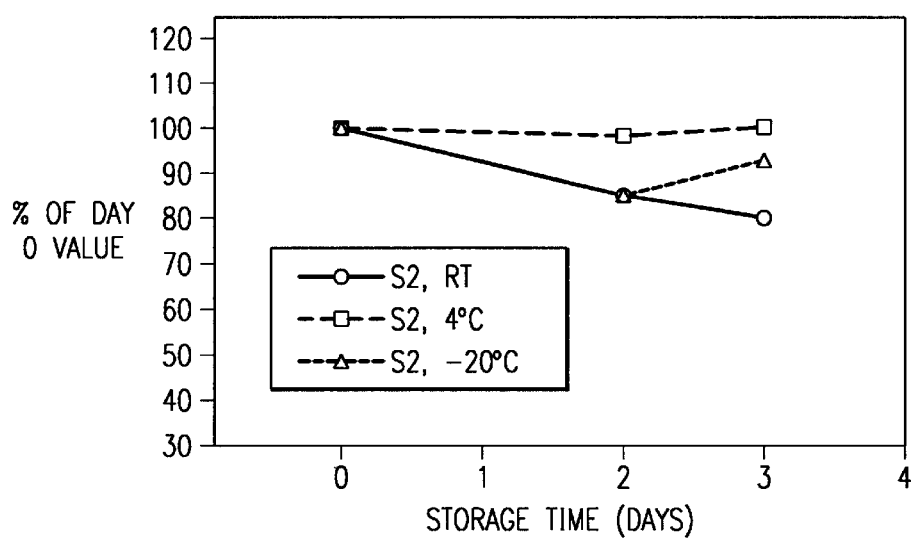
Figure 5C:
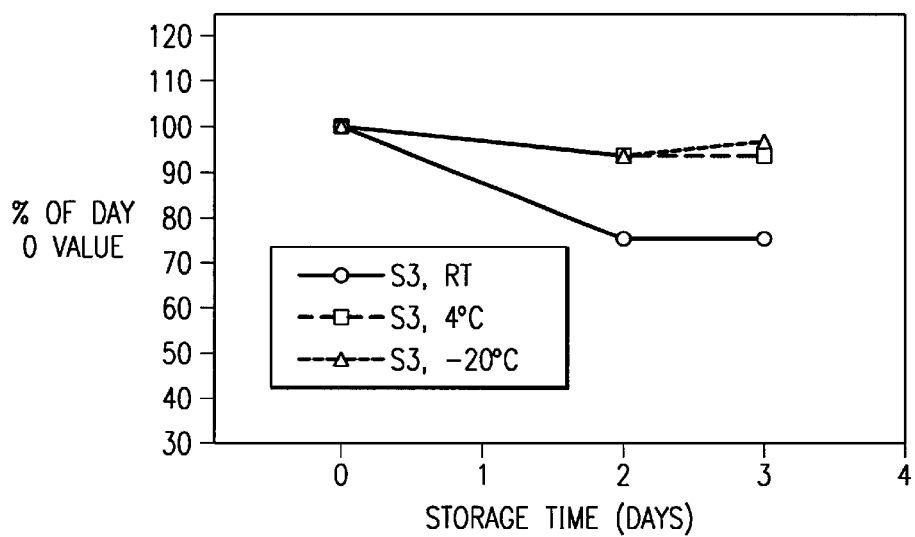

FIGS. 5A–5C. Stability of IGFBP-3 Complex Analysed by ELISA-2.

Replicate aliquots of three different samples (S1=FIG. 5A, S2=FIG. 5B, S3=FIG. 5C) stored at various temperature and analysed as indicated. Percent changes from the day 0 value are shown.

Figure 6A:
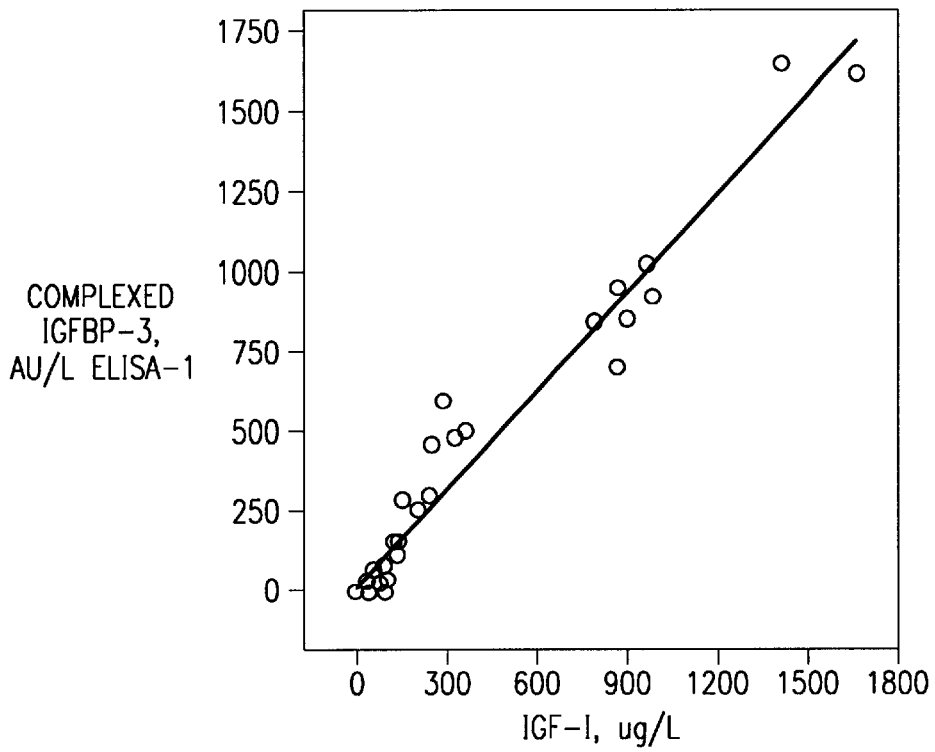
Figure 6B:
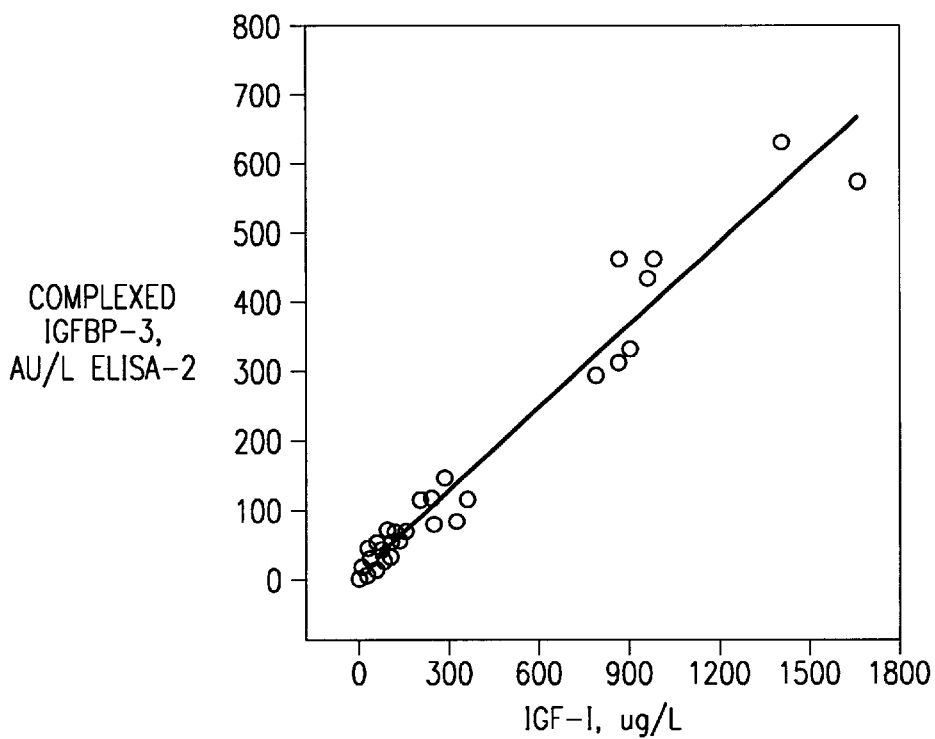

FIGS. 6A–6B. Comparison of IGFBP-3 Complex with IGF-I.

EDTA plasma samples from subjects with untreated GHRD (n=11) and age-matched normal subjects (n=16), and serum samples from adults with acromegaly (n=8) or GHD (n=5) were assayed for IGF-I and IGFBP-3 complex by ELISA-1 (FIG. 6A) and ELISA-2 (FIG. 6B). Values are the mean of duplicate measurements.

Figure 7A:
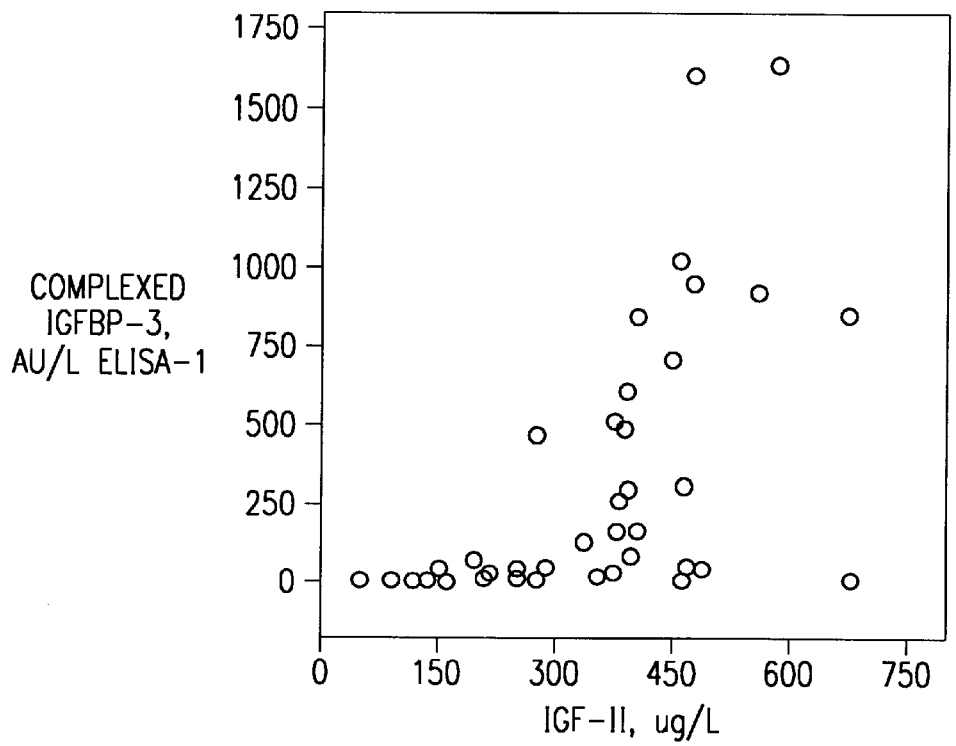
Figure 7B:
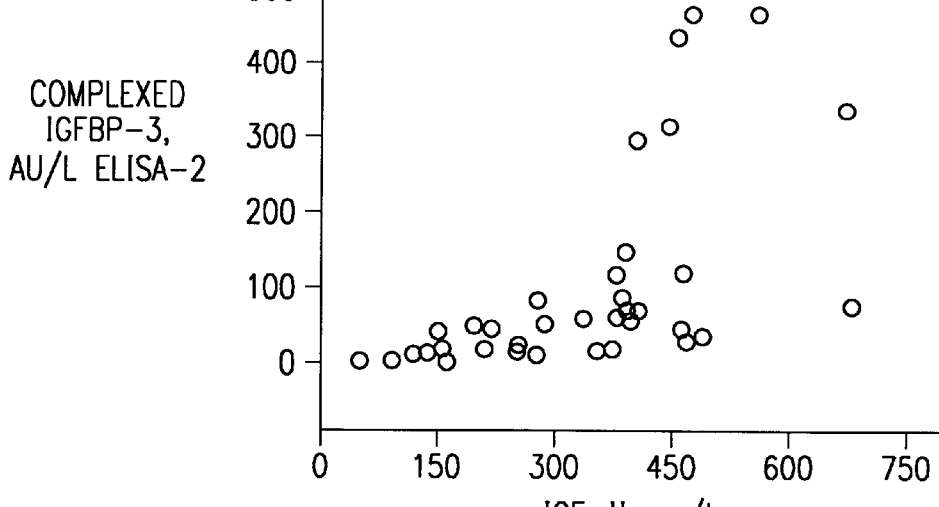

FIGS. 7A–7B. Comparison of IGFBP-3 Complex with IGF-II.

EDTA plasma samples from subjects with untreated GHRD (n=11) and age-matched normal subjects (n=16), and serum samples from adults with acromegaly (n=8) or GHD (n=5) were assayed for IGF-II and IGFBP-3 complex by ELISA-1 (FIG. 7A) and ELISA-2 (FIG. 7B). Values are the mean of of duplicate measurements.

Figure 8A:
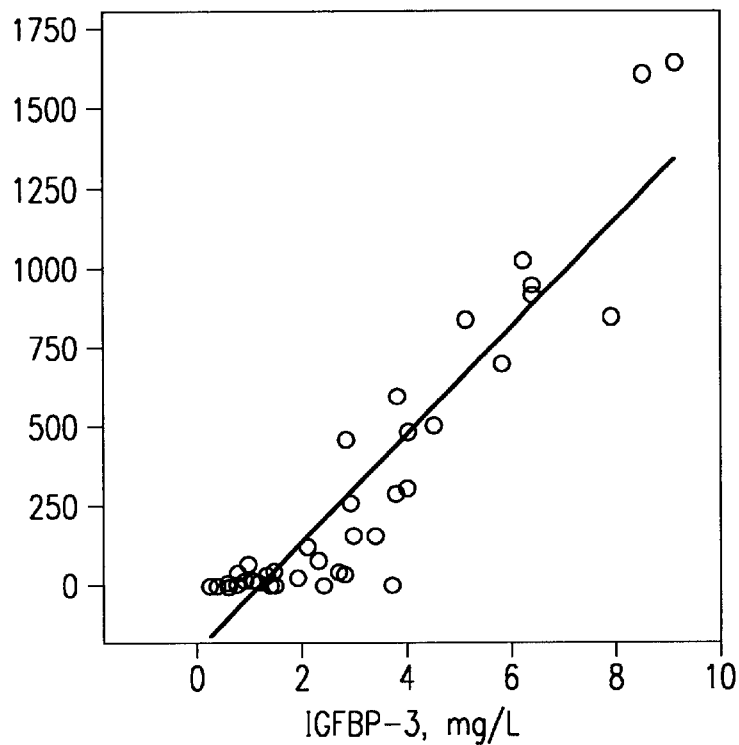
Figure 8B:
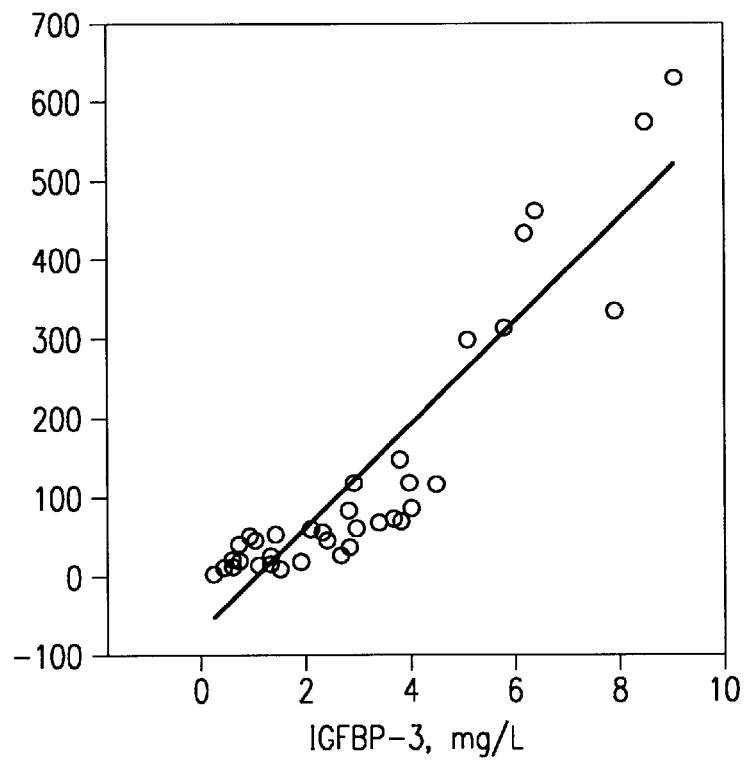

FIGS. 8A–8B. Comparison of IGFBP-3 Complex with IGFBP-3.

EDTA plasma samples from subjects with untreated GHRD (n=11) and age-matched normal subjects (n=16), and serum samples from adults with acromegaly (n=8) or GHD (n=5) were assayed for IGFBP-3 and IGFBP-3 complex by ELISA-1 (FIG. 8A) and ELISA-2 (FIG. 8B). Values are the mean of duplicate measurements.

Figure 9A:
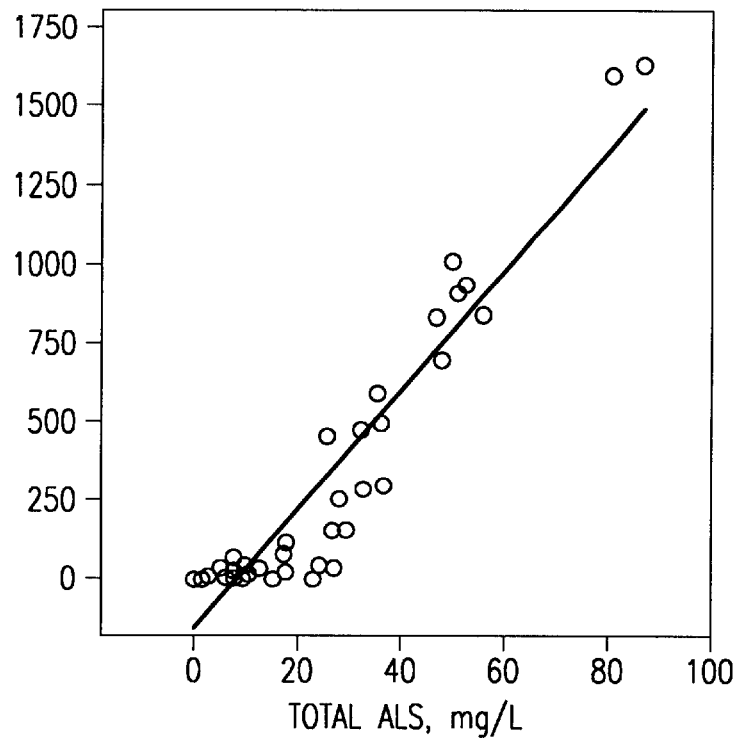
Figure 9B:
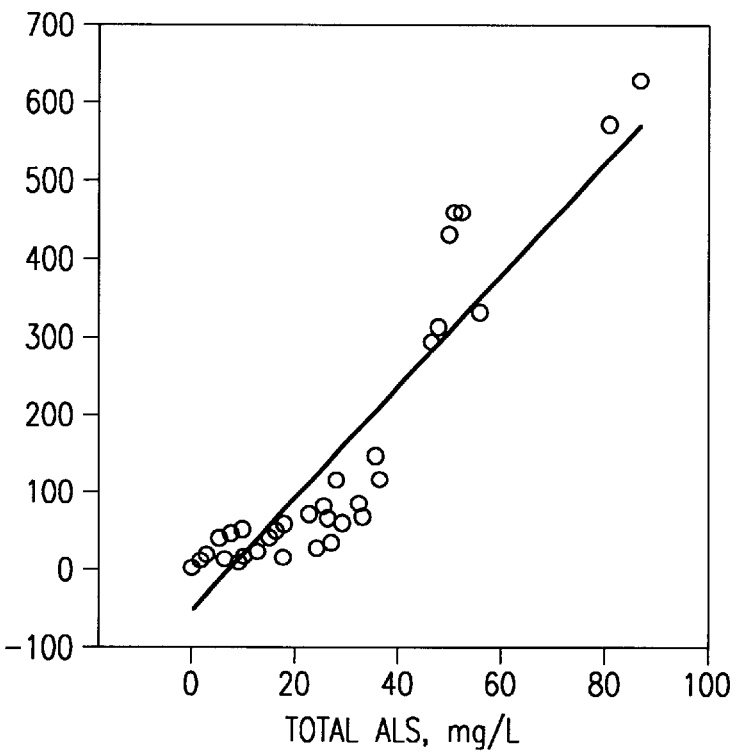

FIGS. 9A–9B. Comparison of IGFBP-3 Complex with total ALS.

EDTA plasma samples from subjects with untreated GHRD (n=11) and age-matched normal subjects (n=16), and serum samples from adults with acromegaly (n=8) or GHD (n=5) were assayed for total ALS and IGFBP-3 complex by ELISA-1 (FIG. 9A) and ELISA-2 (FIG. 9B). Values are the mean of duplicate measurements.

Figure 10:
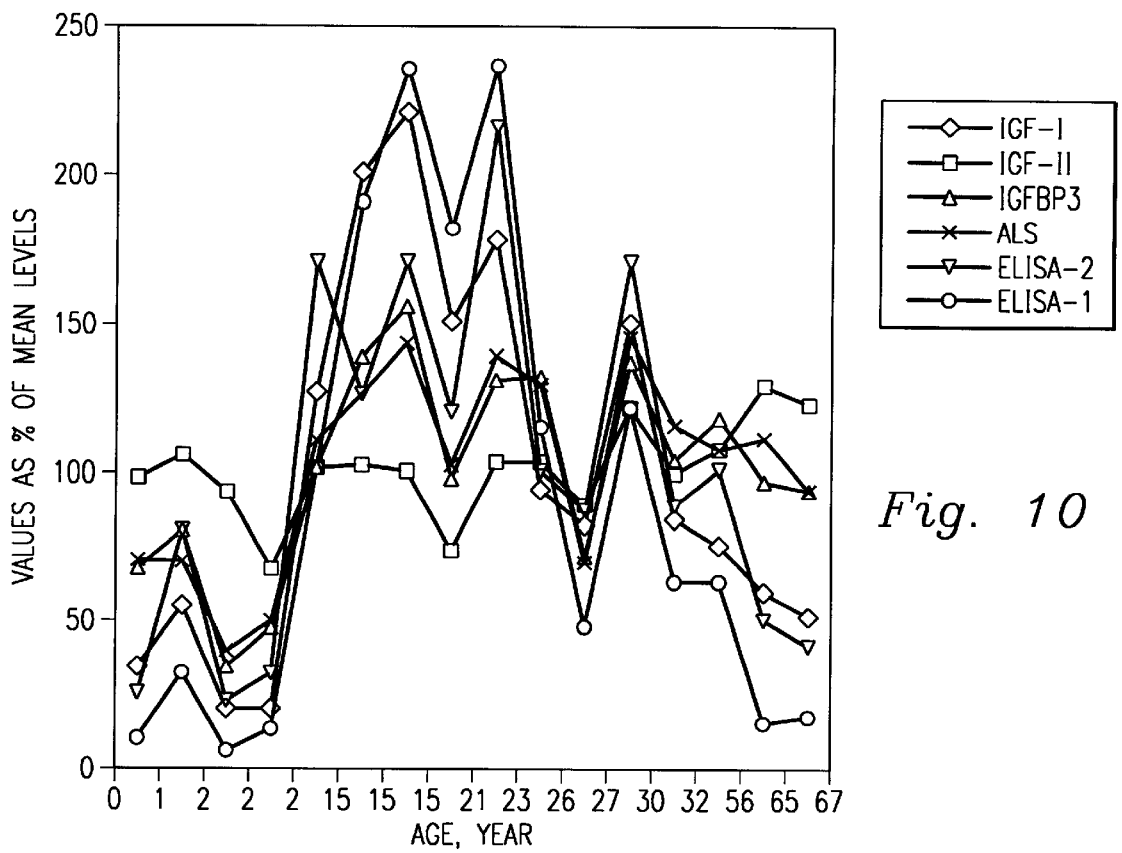

FIG. 10. IGF-axis Components Levels versus Age.

IGF-I, IGF-II, IGFBP-3, ALS and IGFBP-3 complex levels by ELISA-1 and ELISA-2 were measured in EDTA-plasma samples obtained from 16 normal subjects. For each analyte, the individual sample values as a percentage of the corresponding mean values are plotted versus age.

Figure 11:
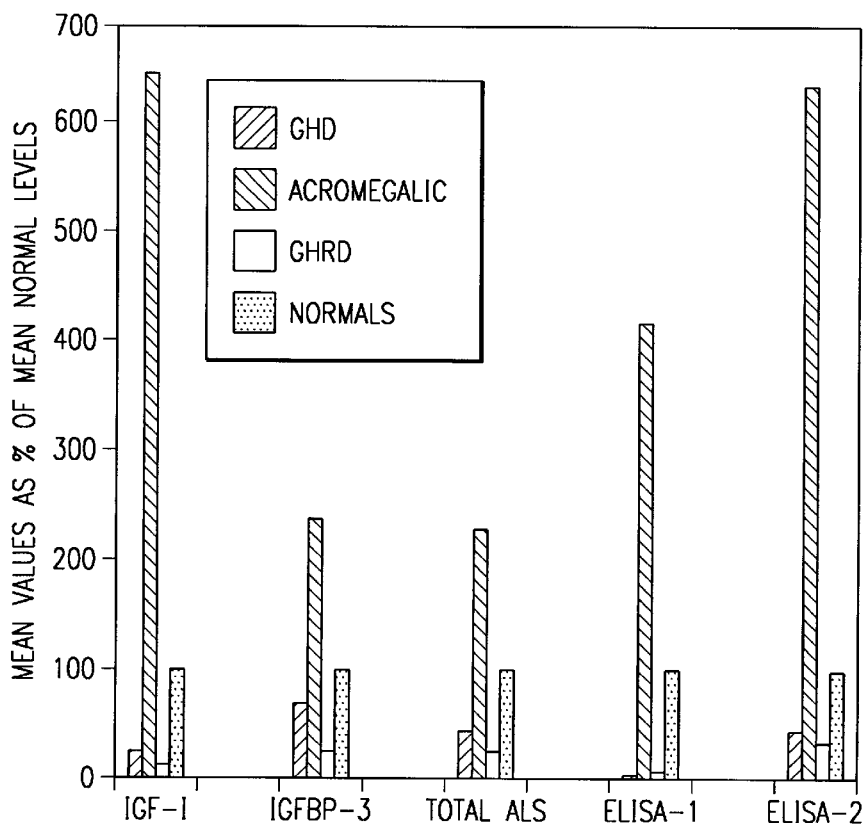

FIG. 11. IGF-Ixis Component Levels as a Percentage of the Mean of Normal Values.

EDTA plasma samples from subjects with untreated GHRD (n=11) and age-matched normal subjects (n=16), and serum samples from adults with acromegaly (n=8) or GHD (n=5) were assayed for IGF-I, IGF-II, IGFBP-3, total ALS and IGFBP-3 complex by ELISA-1 and ELISA-2. The mean concentrations of each analyte measured in each sample group as a percentage of the corresponding mean of the normal values (considered as 100%) are shown.

FIGS. 12A–12F. Distribution Plot of IGF-axis Components and IGFBP-3 Complex

Figure 12A:
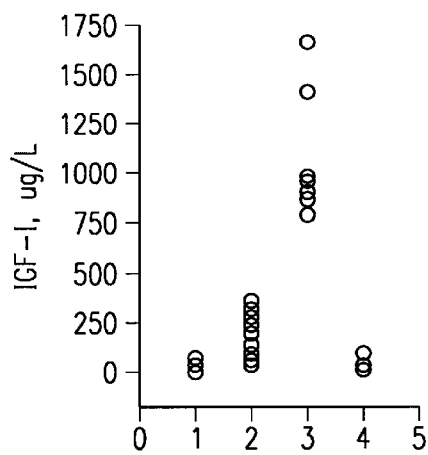
Figure 12B:
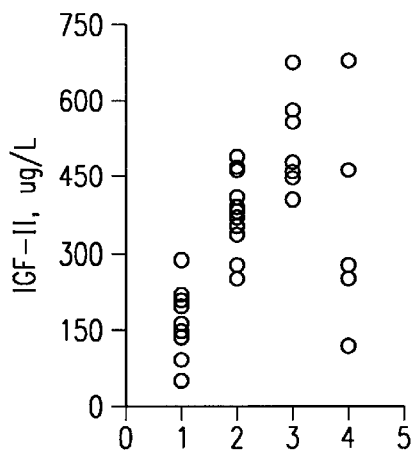
Figure 12C:
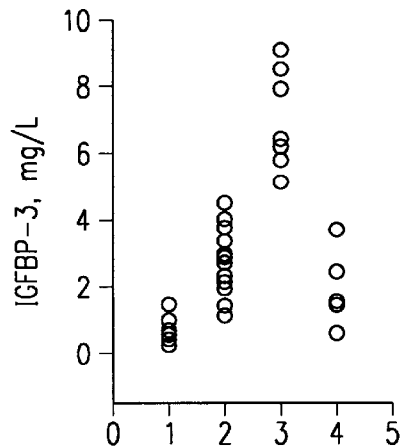
Figure 12D:
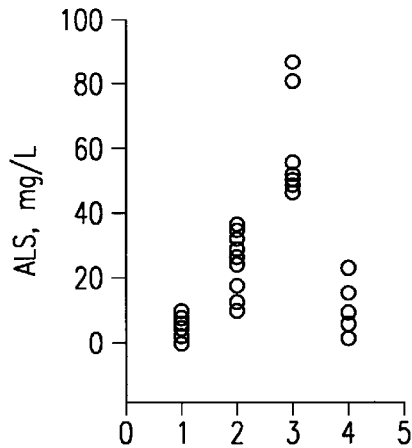
Figure 12E:
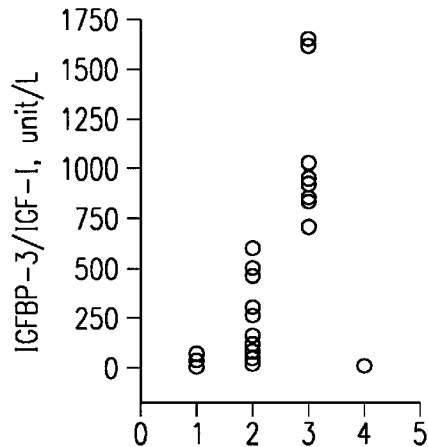
Figure 12F:
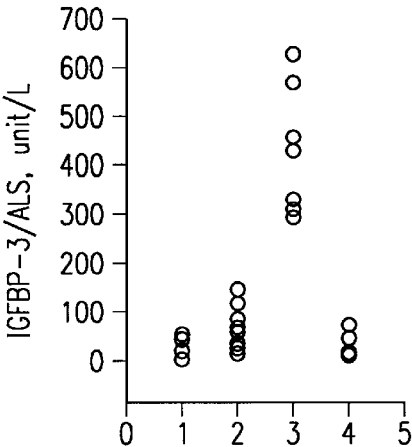

EDTA plasma samples from subjects with untreated GHRD (n=11) and age-matched normal subjects (n=16), and serum samples from adults with acromegaly (n=8) or GHD (n=5) were assayed for IGF-I (FIG. 12A), IGF-II (FIG. 12B), IGFBP-3 (FIG. 12C), total ALS (FIG. 12D) and IGFBP-3 complex by ELISA-1 (FIG. 12E) and ELISA-2 (FIG. 12F). Values represent the mean of duplicate measurements.

DETAILED DESCRIPTION OF THE INVENTION

The capture-detection IGFBP complex assay is exemplified herein in two different formats. However, a variety of antibodies are described and mapped and various combinations of antibody pairs or triplets may be employed in the basic capture-detection assay format. The following examples describe the assays, epitope mapping and antibodies of the invention.

EXAMPLE 1

MATERIALS

A. SAMPLES

EDTA-plasma samples from subjects with untreated GBRD (5 males age 1–32 yr, mean age 17±14.5, and 6 females age 2.3–65 yr, mean age 29.9±25) and age-matched normal controls (8 males age 1–27 yr, mean age 13.3±10.4, and 8 females age 2–67 yr, mean age 36.6±23.7) were obtained from Dr. Jaime Guevara-Aguirre, Institute of Endocrinology, Metabolism and Reproduction, Quito, Ecuador. Ecuadorian GHRD patients were selected for this study since they have extremely low levels of IGF-I and IGFBP-3 (20). The sample collection protocol was approved by the Ethics Committee of the Institute of Endocrinology, Metabolism and Reproduction (Quito-Ecuador) in compliance with the laws and regulations of the United States and Ecuador. All subjects and/or guardians signed Spanish versions of the approved informed consent forms. These samples were stored at −70° C. until use.

Serum samples from consenting adults with acromegaly (n=8) and GH deficiency (n=5) were kindly provided by Dr. John Miell, Department of Medicine, Kings College School of Medicine, London, England. Randomly selected fresh serum samples (n=42) were obtained from Clinical Laboratories in Canada. These samples were residuals from routine clinical test samples and were from an adult population. Upon collection, blood samples were allowed to clot, separated and, after clinical testing, the residuals stored at 4° C. were used for these studies within 48 hours.

B. REAGENTS

Recombinant human IGF-I and IGF-II were obtained from GROPEP, PTY, LTD. (Adelaide, Australia) and recombinant non-glycosylated IGFBP-3, was obtained from CELTRIX PHARMACEUTICAL, INC. (Santa Clara, Calif.). Recombinant human IGFBP-2, and IGFBP-4 through IGFBP-6 were purchased from AUSTRAL BIOLOGICALS (San Roman, Calif.). IGFBP-1 was purified from human amniotic fluid and calibrated against pure recombinant human IGFBP-1 obtained from DSL (Webster, Tex.). Other materials and chemicals were obtained as described (40, 41). Purified human ALS was obtained from DSL (Webster, Tex.) as described elsewhere (15). $^{125}$I-IGFBP-3 ($5\times10^6$ CPM/mL of 0.1 M NaPO4, pH 7.4) was obtained from DSL (Webster, Tex.). HRP-labelled streptavidin was purchased from AMERSHAM INTERNATIONAL (Buckinghamshire, England).

Horseradish peroxidase (IP) was obtained from SCRIPPS LABORATORIES (San Diego, Calif.). Tetramethylbenzidine peroxidase (TMB/$H_2O_2$) substrate system was from KIRKEGAARD AND PERRY LABORATORIES, INC. (Gaithersburg, Md.). Sulfosucci nimidyl-6-(biotinamido) hexanoate (NHS-LC-Biotin) was from PIERCE CHEMICAL CO. (Rockford, Ill.). All other chemical reagents were of highest quality and were obtained from SIGMA CHEMICAL CO. (St. Louis, Mo.), or AMRESCO, INC. (Solon, Ohio). Micro-titration strips and frames were products of COSTAR (Cambridge, Mass.).

C. ASSAY BUFFERS

The IGFBP-3/IGF-I (ELISA-1) and IGFBP-3/ALS (ELISA-2) assays described below are based on similar principles and identical components except for the antibody combination and selection of the assay buffer. The buffers were as follows:

ELISA-1 assay buffer—0.05 molar Tris-maleate, pH 7.0, 9 g/L NaCl, 5 g/L BSA, 0.001 molar sodium EDTA, 0.5 ml/L Tween 20, 0.1 g/L thimerosal.

ELISA-2 assay buffer—0.05 molar Tris-maleate, pH 7.0, 0.9 g/L NaCl, 20 g/L BSA, 0.5 g/L bovine gama globulin, 25 ml/L normal goat serum, 100 mg/L PMSF, 0.5 ml/L Tween 20, 0.1 g/L thimerosal.

Zero standard matrix buffer—0.05 molar sodium phosphate, pH 7.4, 9 g/L NaCl, 1 g/L BSA, 0.005 molar sodium EDTA, 2.5 ml/L trasylol, 0.1 g/L thimerosal.

Antibody-HRP conjugate concentrate buffer—0.02 molar sodium phosphate, pH 7.0, 9 g/L NaCl, 1 g/L $CaCl_2$, 5 g/L BSA, 0.1 g/L thimerosal.

Stopping solution—0.2 molar sulphuric acid in deionized water.

Coating Buffer—50 mM Tris, 0.1% NaAzide, pH 7.8

Wash Buffer—0.05% Tween 20, 5 mM Tris, pH 7.4

Blocking Buffer—50 mM Tris, 1% BSA, 0.025% NaAzide, pH 7.4

D. ANTIBODIES

Methods for preparation of both monoclonal antibodies and polyclonal antibodies are now well established (49). For this invention, the monoclonal antibodies were generated in mice and the polyclonal antibodies were raised in goats. The antibodies could have been raised in various species however, including but not limited to, mouse, rat, rabbit, goat, sheep, donkey, horse, etc. The anti-IGF and anti-IGFBP-3 were raised against unglycosylated recombinant human IGF-I, IGF-II or IGFBP-3 (see Table 1 for antibody names and characteristics). Anti-ALS antibodies were raised against synthetic unique N- and C-terminal regions of human ALS (15). The ALS peptides were conjugated to ovalbumin using glutaraldehyde, mixed with complete Freund's adjuvant and injected into goats (0.1 mg/injection) using a monthly boost and bleed schedule. The ALS peptides were prepared using a Model 430A APPLIED BIOSYSTEMS (Foster City, Calif.) peptide synthesizer (SYNPEP CORP, Dublin, Calif.) and purified by high-performance reverse phase liquid chromatography (HPLC). IGF-I, IGF-II and IGFBP-3 antigens were injected as above without modification.

TABLE 1

Immunogens, Antibody names and Characteristics

| Immunizing Agent | Antibody Name | Characteristics |
|---|---|---|
| recombinant unglycosylated IGFBP-3 | B1 to B10 | ten anti-IGFBP-3 monoclonal antibodies |
| recombinant unglycosylated IGFBP-3 | pB11 | anti-IGFBP-3 polyclonal antibody |
| recombinant unglycosylated human IGF-I | I-1 | anti-C-terminal-IGF-I monoclonal antibody |
| recombinant unglycosylated human IGF-I, | I-2 | anti-N-terminal-IGF-I monoclonal antibody |
| recombinant unglycosylated IGF-II | pI-3 | anti-IGF-II polyclonal antibody |
| synthetic unique N-terminal ($ALS_{1-34}$) region of human ALS | pA-1 | anti-N-terminal-ALS-peptide polyclonal antibody |
| synthetic unique C-terminal ($ALS_{551-578}$) region of human ALS | pA-2 | anti-C-terminal-ALS-peptide polyclonal antibody |

For the development of monoclonal antibodies, splenocytes from appropriately immunized BALB/c mice were fused with myeloma cells by the polyethylene glycol method. The viable hybridomas were selected, screened and propagated. The supernatants from selected clones were screened against the corresponding analyte by ELISA technique. The positive hybridomas were cloned by limiting dilution and clones secreting specific antibodies were used for ascites production. All monoclonal antibodies were affinity purified on protein A columns and appropriately screened for specificity using well established western-immunoblot methods (50).

Polyclonal antibodies were first purified by affinity chromatography over gel columns containing the immobilized corresponding immunogen and the antibody fractions fuirther purified by chromatography over Protein-A columns. As outlined below, the specificity of the antibodies was further substantiated by immunoassay cross-reactivity studies. All antibodies were produced, characterized and purified by DSL, INC. (Webster, Tex.). The anti-IGF-I, anti-IGF-II, anti-ALS and the anti-IGFBP-3 polyclonal antibodies are highly specific for the corresponding analyte (15, 37, 38, 39) and have been employed in corresponding ELISAs manufactured by DSL INC., (Webster, Tex.). The anti-IGFBP-3 monoclonal antibodies are also highly specific for IGFBP-3 and are currently under evaluation for development of additional novel IGFBP-3 ELISAs.

EXAMPLE 2

METHODS: PREPARATIVE ASSAY PROCEDURES

Antibody coating to micro-titre wells was performed at a concentration of 2.5–30 mg/L, unless otherwise indicated, using previously published methods (40). In brief, 0.1–0.2 mL of the antibody solution (5–10 mg/L) was added to each micro-titre well and allowed to incubate overnight at room temperature. The wells were then washed once with the wash solution and 0.2 mL/well of the blocking solution was added and allowed to incubate for 1 hour as above. The wells were washed once prior to use, or stored for up to 1 week in the blocking buffer at 4° C.

IGFBP-3 coating to micro-titre wells was performed as described above, except that IGFBP-3 was coated at a concentration of 0.25–2 mg/L.

Antibody coupling to HRP was performed as previously described (41). The coupling reaction involved initial activation of the enzyme with sulfosuccinimidyl 4-(N-maleimidomethyl) cylcohexane-1-carboxylate (SMCC) and its subsequent conjugation to 2-iminothiolane activated antibody. The stock HRP-conjugated antibody solution was stored at 4° C. in the dark and appropriately diluted (at least 1000-fold) in the appropriate assay buffer prior to use.

Antibody coupling to biotin was performed as previously described (42). Biotinylation was performed at about a 150-fold molar excess of NHS-LC-Biotin added to 0.5 mg/mL of the antibody solution. The unconjugated biotin was removed by dialysis at 4° C. for 24 hours against several changes of 0.1 molar sodium bicarbonate, pH 8.3, containing 9 g/L of NaCl and 0.25 g/L of sodium azide. The stock antibody-biotin conjugate solution stored at 4° C. and appropriately diluted in 0.05 molar $NaPO_4$, pH 7.2, containing 9 g/L of NaCl, 2 g/L of BSA and 1.0 mL/L of the antibacterial/antifungal preservative Proclin 300 (SIGMA) prior to use.

A pool of fresh serum samples was assigned 100 arbitrary units per litre (AU/L) of IGF-binding protein complex (IGFBP-3 complex) and used for ELISA-1 and ELISA-2 standardization. Standards were prepared by appropriately diluting the serum pool in the zero standard matrix buffer to give reference standard values of 0.78, 1.56, 6.25, 25 and 50 AU/L of IGFBP-3/IGF-I complex, and 3.13, 6.25, 12.5, 25, and 50 AU/L of IGFBP-3/ALS complex for use in ELISA-I and ELISA-2, respectively. The standards were stable for up to 24 hours at 4° C. and greater than 2 months at −20° C. or lower. The quality control samples used were also appropriately diluted serum pools. The nominal concentrations of the control samples were established by analysing them in IGFBP-3 complex ELISA-1 and ELISA-2.

EXAMPLE 3

METHODS. IGFBP-3 EPITOPE MAPPING

A. SIMULTANEOUS BINDING OF ANTI-IGFBP ANTIBODIES

The anti-IGFBP-3 antibodies (B1 to B10) were evaluated for simultaneous binding (pairing) to IGFBP-3. In brief each antibody was immobilized onto micro-titre wells at 500 ng/100 μl/well and reacted with IGFBP-3 at 0.0 to 100 μg/L (25 μl/well standards plus 100 μl/well assay buffer). After 1 hour shaking (500–700 rpm) incubation at room temperature (RT), wells were washed four times and reacted with each remaining HRP4abelled anti-IGFBP-3 antibody as above for 30 minutes. Stock HRP-antibodies were diluted about 10,000-fold in the assay buffer and used at 100 μl/well (about 5 ng antibody). After washing, the reaction was developed by 10 minute incubation of the wells with the $TMB/H_2O_2$ substrate solution (100 μl/well) and addition of the stopping solution as described below. Maximum increase in optical density (OD) of ≦3×background (zero standard signal) between 3×background to 1 OD, between 1 OD to ≦2 OD, and ≧2 OD were ranked as indication of no simultaneous binding (pairing) to IGFBP-3, weak pairing, moderate pairing and strong pairing, respectively.

B. COMPETITIVE BINDING OF ANTI-IGFBP ANTIBODIES

The anti-IGFBP-3 antibodies (B1 to B10) were also evaluated for competitive binding to IGFBP-3. In brief, each biotinylated antibody at a predetermined dilution was mixed with increasing concentrations of each remaining urdabelled antibody (0–50 μg/ml) and added (50 μL antibody plus 100 μl assay buffer) to triplicate wells pre-coated with IGFBP-3 (about 75 ng/well). After 2 hours shaking incubation, the wells were washed and developed by 30 minute reaction with HRP-labelled streptavidin (100 μL/well at 2000-fold dilution in the assay buffer) followed by $TMB/H_2O_2$ and addition of the stopping solution. Decrease in OD of ≦20%, 20–60%, and ≧60% were ranked as indicative of non-interfering, moderately interfering and strongly interfering binding of the antibody pair to IGFBP-3.

C. EFFECTS OF IGF OCCUPANCY ON ANTI-IGFBP BINDING

The effect of IGF occupancy of IGEBP-3 on binding of anti-IGFBP-3 antibodies (B1 to B10) was also evaluated. In brief, $^{125}$I-IGFBP-3 ($1\times10^6$ cpm/mL) was mixed with 0.0 to 0.75 μg/mL IGF-I or IGF-II (in ELISA 1 assay buffer), incubated for 2 hours at RT, and 100 μL/well were added in triplicate to anti-IGFBP-3 antibody coated wells. After 2 hours RT incubation, wells were washed three times with $dH_2O$ and counted for bound radioactivity in a Packard RIASTAR gamma counter from PACKARD CANADA (Mississauga, Ontario). An antibody binds at or near the IGF binding site when its IGFBP-3 binding signal (CPM) is decreased by at least 30% in response to IGFBP-3 pre-incubation with IGFs.

D. SIMULTANEOUS BINDING OF ANTI-IGFBP AND ANTI-IGF OR -ALS ANTIBODIES

Native serum IGFBP-3 complex was also evaluated for simultaneous binding to anti-IGFBP-3 antibodies (B1-B10) in combination with anti-IGF4 antibodies (I-1, I-2), anti-IGF-II antibodies (pI-3) or anti-ALS antibodies (pA-1, pA-2) in pair-wise "mix-antibody" sandwich ELISA. In brief, a pool of human serum was prepared by mixing aliquots from 15 different serum samples. Micro-titration strips coated with each antibody were incubated, in quadruplicates, with 50 μL/well of the serum pool or standard matrix buffer and 100 μL/well of the appropriate assay buffer for 2 hours at RT as above. After washing, each quadruplicate set of serum pool/zero standard matrix buffer treated wells were then incubated with 100 μl/well of each of HRP-labelled anti-IGF-I, anti-IGF-II, or anti-ALS antibodies for 30 min at RT. After washing, the reaction was developed by 10 min incubation with $TMB/H_2O_2$ substrate and addition of the stopping solution. Increase in OD of ≦3×background (zero standard signal), between 3×background to 1 OD, and between 1–≧2 OD indicates no binding, moderate binding or strong simultaneous binding of the two antibodies to complexed serum IGFBP-3, respectively. Mix-antibody combinations showing the strongest signal were selected for IGFBP-3 complex ELISA development as described below.

EXAMPLE 4

EPITOPE MAP OF COMPLEXED IGFBP-3

Detailed information on epitopes recognized by IGFBP-3 monoclonal antibodies was obtained by evaluating all possible twosite (capture-detection) combinations in pair-wise sandwich ELISA. The spacial distribution of epitopes recognized by each antibody in relation to others was then evaluated in pair-wise competitive ELISA which evaluates binding of a given antibody to IGFBP-3 in the presence of excess amounts of each of the remaining antibodies. The latter provided information on whether an epitope recognized by one antibody was distinct enough to allow non-interfering (independent) binding of a second antibody or whether the epitope recognized were completely or partially overlapping, resulting in binding interferences.

In the third series of experiments, interference in antibody binding to IGFBP-3 by IGF-I or IGF-II was evaluated. This identified antigenic domains at or near the IGF binding site and was assessed by monitoring binding of solid-phase antibodies to IGFBP-3 before and after pre-incubation with radio-labelled IGFs. Finally, the ability of IGFBP-3 antibodies for binding to serum IGFBP-3 complex in pair-wise combination with anti-IGF-I, IGF-II and ALS antibodies was evaluated in "mix antibody" sandwich ELISA. In similar experiments, simultaneous binding of complexed IGFBP-3 to anti-IGFs paired with anti-ALS antibodies was also examined.

As shown in Table 2, assessment of the 10 IGFBP-3 antibodies (B1 to B10) in sandwich ELISA identified 31 of the possible 100 combinations. The binding patterns appear to cluster into four antigenic regions based on reacting antibody combinations and the strength of pairing signal generated. The antibodies were grouped as follows: Group I included B5, B6 and B8; Group II included B1, B2, B4, and B7; Group III included B3; and Group IV included B9. Antibodies in the same group did not bind simultaneously to IGFBP-3 in sandwich ELISA, but demonstrated weak to strong pairing with antibodies in other groups.

TABLE 2

Pair-wise evaluation of IGFBP-3 antibodies in sandwich ELISA - Simultaneous "two-site" antibody binding patterns to IGFBP-3 are shown. Letters, "n" indicates no simultaneous binding; W, M, S, weak, moderate and strong pairing signal, respectively. B9 and B10, no pairing; B9, strong pairing with B3 only.

| Detection-antibody | Capture-antibody | | | | | | | | | |
|---|---|---|---|---|---|---|---|---|---|---|
| | B1 | B2 | B3 | B4 | B5 | B6 | B7 | B8 | B9 | B10 |
| B1 | | n | M | n | n | n | n | n | n | n |
| B2 | n | | M | n | W | n | n | n | n | n |
| B3 | M | M | | M | S | S | W | S | n | n |
| B4 | n | n | M | | M | M | n | M | n | n |
| B5 | M | M | S | M | | n | n | n | n | n |
| B6 | M | M | S | M | n | | M | n | n | n |
| B7 | n | n | M | n | n | M | | M | n | n |
| B8 | M | M | S | M | n | n | n | | n | n |
| B9 | n | n | S | n | n | n | n | n | | n |
| B10 | n | n | n | n | n | n | n | n | n | |

Pairing of antibodies in group I and group II appear to depend, to some extend, on whether a given antibody was used for coating or detection. This is presumably due to suboptimal antibody concentrations and/or epitope conformational changes induced by binding of the first antibody to IGFBP-3. The strongest two-site binding signals were generated between antibodies in Group I and Group III (B3). B9 and B10 were unable to form sandwich with each other or with remaining antibodies. B9 demonstrated strong binding to IGFBP-3 only when used as the detection-antibody in combination with B3.

A clearer pictured emerged when antibodies were evaluated for binding to solid-phase IGFBP-3 in pair-wise competitive ELISA (Table 3). In these experiments, non-pairing, moderately pairing and strongly pairing antibodies identified in Table 2, appeared to compete with one another strongly, moderately or not-at all, respectively. Only combinations of Group I with Group III antibodies could bind simultaneously to IGFBP-3 without any interference. Again, B9 could also bind strongly to IGFBP-3 when B3 was present.

TABLE 3

Pair-wise evaluation of IGFBP-3 antibodies in competitive ELISA - Simultaneous competitive binding patterns to IGFBP-3 are shown. Letters, "N" indicates non-interfering "simultaneous" binding; S and M, strong and moderate binding interferences, respectively. n, no signal as detection, no interference as competing antibody. C, B9 binding in the presence of B3 only.

| Competing antibody | Detection-antibody | | | | | | | |
|---|---|---|---|---|---|---|---|---|
| | B1 | B2 | B3 | B4 | B5 | B6 | B7 | B8 |
| B1 | | S | M | S | M | M | S | M |
| B2 | S | | M | S | M | M | S | M |
| B3 | M | M | | M | N | N | M | N |
| B4 | S | S | M | | M | M | S | M |
| B5 | M | M | N | M | | S | M | S |
| B6 | M | M | N | M | S | | M | M |
| B7 | S | S | M | S | M | M | | M |
| B8 | M | M | N | M | S | S | M | |
| B9 | n | n | C | n | n | n | n | n |
| B10 | n | n | n | n | n | n | n | n |
| PSA Ab | n | n | n | n | n | n | n | n |

Binding of Group I antibodies to IGFBP-3 were significantly inhibited by pre-incubation of IGFBP-3 with IGF-I or IGF-II. This positioned Group 1 recognition epitopes at or near IGF binding site. In repeat experiments, binding of Group I antibodies to IGFs/IGFBP-3 complexes decreased by more than 50%, whereas activity of Group II, and Group III antibodies as well as the IGFBP-3 polyclonal antibody (pB11) remained relatively unchanged (Table 4, FIG. 2). Binding of B9 was about 2-fold higher than that of an irrelevant antibody (anti-PSA) and was not affected by IGF binding to IGFBP-3. B10 was non-reactive as it generated similar signal to that of the anti-PSA antibody.

TABLE 4

Inhibition of Antibody binding to IGFBP-3 by IGF-I and IGF-II - Binding of iodinated rIGFBP-3 to antibody coated wells examined with or without pre-incubation with IGF-I or IGF-II. Values are the mean (SD) of three measurements.

| | Mean CPM (SD) | | |
|---|---|---|---|
| Antibody | IGFBP-3 | IGFBP-3 + IGF-I | IGFBP-3 + IGF-II |
| B1 | 9192 (416) | 8356 (432) | 8736 (264) |
| B2 | 9589 (1035) | 9633 (1093) | 9684 (196) |
| B3 | 1617 (151) | 16803 (1051) | 17913 (82) |
| B4 | 5846 (384) | 6156 (560) | 6235 (78) |
| B5 | 5414 (142) | 2326 (25) | 2060 (214) |
| B6 | 5910 (310) | 1832 (24) | 1435 (64) |
| B7 | 4830 (165) | 4305 (376) | 4698 (49) |
| B8 | 6066 (32) | 1746 (23) | 2110 (39) |
| B9 | 1257 (141) | 960 (71) | 1269 (69) |
| B10 | 706 (25) | 495 (50) | 602 (63) |
| pB1 11 | 28466 (902) | 30485 (503) | 30767 (357) |
| PSA Ab | 594 (115) | 457 (38) | 483 (13) |

In two-site "mix-antibody" ELISA (anti-IGFBP paired with anti-ALS or anti-IGF), antibodies in Group II and Group III demonstrated simultaneous binding to the naturally occurring (native) serum IGFBP-3 complex in combination with anti-IGF-I (I1) or an anti-ALS (pA-1) antibodies used for detection. The strongest pairing signal was observed with the B2/pA-1 antibody pair and the B3/I1 antibody pair. No simultaneous binding to serum IGFBP-3 complex was observed when the anti-IGF-I antibodies were evaluated against anti-ALS antibodies in all possible mix-antibody combinations. Bindings of other possible mix-antibody combinations were similar to that involving the negative control anti-PSA antibody (Table 5).

TABLE 5

Pair-wise evaluation of IGFBP-3 antibodies in combination with
anti-IGF-I or anti-ALS antibodies for binding to IGFBP-3
complexes - Simultaneous "two-site" mix-antibody
binding patterns to serum IGFBP-3 complex are shown. Letters,
"n", no simultaneous binding; W, M, S, weak, moderate
and strong pairing signals, respectively.

| Capture-antibody | Detection-antibody | | | | |
|---|---|---|---|---|---|
| | I-1 | I-2 | pI-3 | pA-1 | pA-2 |
| B1 | W | n | n | W | n |
| B2 | M | n | n | M | n |
| B3 | W | n | n | M | n |
| B4 | W | n | n | W | n |
| B5 | n | n | n | n | n |
| B6 | n | n | n | n | n |
| B7 | W | n | n | W | N |
| B8 | n | n | n | n | n |
| B9 | n | n | n | n | n |
| B10 | n | n | n | n | n |
| PSA Ab | n | n | n | n | n |

The binding characteristics of the four groups are summarized as follows:

Group I: IGFBP antibodies (B5, B6 and B8) This group of antibodies recognized epitopes that mapped at or near the IGFBP-3 ligand binding site as defined by their binding inhibition in response to IGFBP-3 pre-incubation with the IGFs. These antibodies could not be distinguished from each other as they did not bind simultaneously to IGFBP-3 in sandwich ELISA and strongly competed with each other in competitive binding assays.

By western immunoblot of various IGFBP-3 fragments, two of Group I antibodies (B5 and B8) have been recently shown to recognize epitopes at both N-terminal (IGFBP-$3_{1-97}$) as well as C-termninal (IGFBP-$3_{-200-264}$) regions of IGFBP-3, whereas B6 was found to react only with the N-terminal (IGFBP-$3_{1-97}$) fragment (44). The result of the present study seems to indicate binding of B6 to the C-terminal as well as N-terminal regions of IGFBP-3. B6 strongly inhibited binding of B5 and B8 to IGFBP-3 in pair-wise competitive ELISA, but as with B5 and B8, demonstrated strong "non-overlapping" sandwich formation with B3.

It is also possible that B6 binds to N-terminal sequences that forms part of the IGFBP-3 ligand (IGF) binding site. As the IGF binding site of IGFBP-3 is thought to involve both N- as well as C-terminal sequences, antibodies that bind to such conformational epitopes could compete strongly for binding to the native molecule, but differently to denatured fragments in western immunoblot analysis. However, our findings of ligand binding site specificity for antibodies that reportedly bind to both N- and C-terminal of IGFBP-3 (44) is consistent with the notion that both N- and C-terminal sequences of IGFBP-3 contribute to the formation of IGF-binding site (44, 45).

Group II: IGFBP antibodies (B1, B2, B4, B7)—Although epitopes recognized by Group II antibodies overlapped with those specified by Group-I antibodies, the immuno-reactivity of Group II antibodies was not affected by IGF binding to IGFBP-3. The antigenic cluster recognized by Group II antibodies was therefore, physically mapped to an area on the molecule distant from the IGFBP-3 ligand binding site. Again Group II antibodies could not be distinguished from each other as they appeared to bind to overlapping epitopes. Consistent with our findings is the reported specificity of Group II antibodies for the intermediate sequences of IGFBP-3 (IGFBP-$3_{98-159}$) as evaluated by western immunoblot analysis (44).

Group III: IGFBP Antibody (B3) Only one antibody defined a third epitope. The determinant for this antibody also overlapped with those of Group II, but was distinct from Group I antibodies. B3 formed strong non-competing sandwich assays with antibodies in Group-I. Interestingly, this antibody have been found to recognize an epitope within the N-terminal region of IGFBP-3 (IGFBP-$3_{1-97}$) (44), which according to our findings must not overlap with those of N-terminal IGF-binding region.

Group IV: IGFBP Antibody (B9) A fourth antigenic epitope recognized by B9 appeared to be a distinct conformational epitope that was accessible only after binding of B3 to IGFBP-3. In capture-detection-antibody binding ELISA, Group II and Group III antibodies could bind simultaneously to the native serum IGFBP-3 complexes in combination with the I-1 or pA-1 antibody used for detection. The strongest pairing signal was obtained for the B3/I-1 (ELISA-1) and B2/pA-1 (ELISA-2) combinations. This indicates that even in the native IGFBP-3 ternary complexes, antigenic domains on IGF-I as well as ALS are accessible for antibody binding and can participate in two-site "capture-detection" antibody formation. Consistent with these findings, are the recent observations that binding of rIGF-I to solid-phase IGFBP-3 was detectable by C-terminal specific (D-domain, residues 63–70) anti-IGF-I mouse monoclonal antibodies in sequential binding experiments (46).

Figure 1:
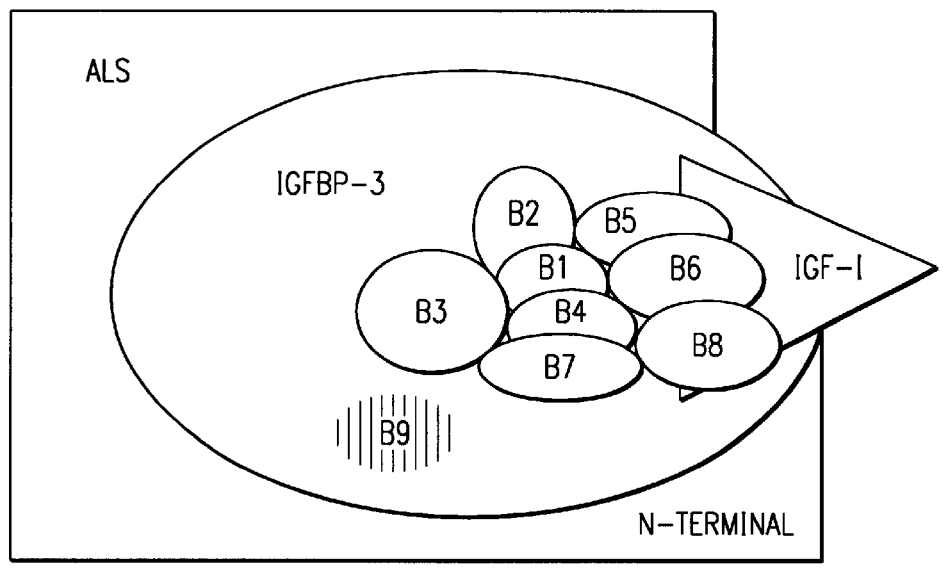
FIG. 1. Epitope Map of IGFBP-3 Complex.

The lack of simultaneous "two-site" binding of the above I-1 and pA-1 to serum IGFBP-3 complex suggests close binding proximity of the N-terminal part of ALS and IGF binding site of IGFBP-3 (FIG. 1). This observation may provide an explanation for the reported finding that ALS binding to IGFBP-3 is an important modulator of IGFBP-3 affinity for the IGF peptides (47). Similar to the effect of antibody B3 on the immuno-reactivity of antibody B9 described above, proximal ALS binding to IGFBP-3 blgand binding site could cause conformational changes, leading to enhanced IGF binding affinity of IGFBP-3.

EXAMPLE 5

Methods: ELISA-1 and -2.

A. ELISA-1

Among possible anti-IGFBP-3/anti-IGF-I combinations, the anti-IGFBP-3 B3 and anti-IGF-I I-1 generated strongest binding signal to serum IGF-binding protein complex when used as capture and detection-antibodies, respectively. The ELISA protocol was optimized as described previously (37, 41).

In the assay, standards or serum samples (0.025 mL of 10–40 fold diluted in the assay zero standard matrix buffer) were added in duplicate to antibody coated wells, followed by addition of the ELISA 1 assay buffer (0.10 mL) and 1 hour incubation at room temperature with continuous shaking. The wells were washed five times and incubated with 0.1 mL/well of the anti-IGF-I-HRP conjugate (diluted in the assay buffer to approximately 0.1–0.25 mg/L) for 1 hour at room temperature. The wells were washed five times with the wash solution, 0.1 mL of the TMB/$H_2O_2$ substrate solution added for an additional 10 min incubation at room temperature. Stopping solution (0.1 mL) was then added and absorbance measured by dual wavelength measurement at 450 nm with background wavelength correction set at 620 nm.

ELISA data were analysed using data reduction packages included in the LAB SYSTEMS microplate reader with cubic spline (smoothed) curve fit. Other statistical analyses were performed using the MICROSOFT EXCEL 97 STATISTICAL PACKAGE by MICROSOFT CORPORATION (USA) on an IBM clone Pentium computer. Descriptive data are presented as the mean and SD unless otherwise specified. Linear-regression analysis was performed by the least-squares method and correlation coefficients were determined by the Pearson method.

B. ELISA-2

Among possible anti-IGFBP-3/anti-ALS combinations, the anti-IGFBP-3 B2 and anti-ALS pA-1 generated the strongest binding signal to serum IGF-binding protein complex when used as capture and detection-antbodies, respectively. The assay protocol was exactly as described above, except that the optimal sample and assay buffer volumes were 25 µl and 50 µl/well, respectively.

C. VALIDATION OF ELISA-1 AND -2.

For validation of IGFBP-3 complex ELISA-1 and ELISA-2, appropriately diluted fresh serum samples were used. In both assays, the lower limit of detection (sensitivity) was determined by interpolating the mean plus 2SD of 12 replicate measurements of the negative control (zero standard matrix buffer). The intra-assay correlation coefficients (CVs) were determined by replicate analysis (n=12) of 3 samples at IGFBP-3/IGF-I levels of 8.6–24.3 AU/L, and IGFBP-3/ALS levels of 6.7–18.7 AU/L; interassay CVs by duplicate measurement of appropriate samples in 7–9 separate runs. Recovery was assessed by adding 50 µL of samples containing different IGFBP-3 complex levels to 450 µl of 10-fold diluted serum samples followed by analysis. Percent recovery was determined by comparison of the amount of added IGFBP-3 complex to the amount measured after subtracting the endogenous IGFBP-3 complex level. Linearity was tested by analysing serum samples diluted first 10-fold, then serially 2–16 fold in the zero standard matrix buffer. IGFBP-3 complex ELISA specificity was analysed by assaying IGF-I (up to 300 µg/L), IGF-II (up to 3000 µg/L), IGFBP-1, 2, 4–6 up to 500 µg/L, and IGFBP-3 up to 4.3 mg/L.

To evaluate IGFBP-3 complex stability, and thus practical use of the assay, aliquots of fresh serum samples (n=3) were stored at RT, 4° C., and −20° C. and then analysed on day 0, 2 and 3 of storage by ELISA-1 and ELISA-2 after 10-fold dilution in the assay zero standard matrix buffer. On the day of analysis, samples were assayed against a new set of standards freshly prepared from a frozen (at −20° C.) aliquot of the stock standard serum pool. Aliquots of a set of standards were also stored at the above temperatures and similarly analysed.

ELISA-1 and -2 results were compared with results obtained from prior art assays. IGF-I, IGF-II, IGFBP-3 and ALS were analysed by immunoassay kits manufactured by DSL (Webster, Tex.). These assays are based on non-competitive ELISA principles performed in antibody coated micro-wells (15, 37, 38, 39) and horseradish peroxidase (HRP) labelled detection-antibodies as described (41).

IGF-I and IGF-II were assayed by the ACTIV™ Non-Extraction IGF-I and IGF-II ELISA (DSL, Webster) which incorporates a sample pre-treatment step to dissociate IGF-I from IGFBPs prior to analysis (43). The sample pre-treatment step involves mixing 20 µl of sample with 1.0 mL of IGF-I acidification buffer followed by 30 min room temperature incubation, and addition of 1.0 mL of the neutralization buffer. The final sample preparation dilution factor was 101-fold and 20 µl of the treated sample is used for IGF analysis. The IGF ELISA kits each have a total incubation time of less than 3 hours and an overall imprecision of less than 10%.

The ACTIVE™ IGFBP-3 ELISA (DSL, Webster) incorporates a 101-fold sample pre-dilution and uses 25 µl of the pre-diluted sample for IGFBP-3 analysis. The assay has a total incubation time of about 3 hours, a standard range of 2–100 µg/L (0.20–10 mg/L after correction for sample dilution factor) and an overall imprecision of less than 10% (39).

The ACTIVE™ Total ALS ELISA (DSL, Webster) incorporates a 101-fold sample pre-treatment step that would result in unfolding of both complexed and uncomplexed ALS, thus allowing measurement of the total ALS levels (15). The sample pre-treatment step involves mixing of 10 µl of sample with 1.0 mL of the sample pre-treatment buffer followed by 30 minute room temperature incubation. The final sample preparation dilution factor was 101-fold and 20 µl of the treated sample is used for Total ALS analysis. The assay has a total incubation time of about 2 hours, a standard range of 6–600 µg/L (0.6–60 mg/L after correction for sample pre-treatment dilution factor) and an overall imprecision of less than 10%.

Absorbance of ELISAs were measured with the LABSYSTEMS MULTISKAN MULTIOFT microplate reader by LABSYSTEMS, (Helsinki, Finland).

EXAMPLE 6.

Results: ELISA-1 and ELISA-2

A. ELISA-1 AND -2.

Based on the above epitope mapping, novel immunoassays for quantisation of circulating IGFBP-3 complexes were developed. Both the IGFBP-3/IGF-I ELISA-1 and the IGFBP-3/ALS ELISA-2 involve a two-site noncompetitive (sequential) immunoreaction and are based on solid-phase anti-IGFBP-3 B3 or B2 antibody paired with detection anti-IGF-I I-I or anti-ALS pA-1 antibodies, respectively.

Optimized protocols were established by evaluating the effects of various technical manipulations on the analytical performance of the assays as previously described (37, 41). A coating antibody concentration of 10 mg/L, a detection-antibody concentration of about 0.1–0.25 mg/L, a 60 minute first and second step room temperature incubations, and a 10 minute substrate development step were selected. Among the variables examined, composition of the assay buffer and coating antibody concentrations had the most obvious effect on sensitivity and dynamic range of the assays.

A typical standard curve and performance characteristics of ELISA-1 and ELISA-2 are summarized in FIGS. 3A–3B and Table 6. Addition of IGF-I (up to 300 µg/L), IGF-II (up to 3000 µg/L), IGFBP-2 and IGFBP-4–6 (up to 500 µg/L), and IGFBP-3 (up to 4.2 mg/L) to the zero standard matrix buffer did not show any cross-reactivity.

TABLE 6

Complex IGFBP-3 ELISA-1 and -2 validation data - No cross reactivity was detected with IGF-I, IGF-II, IGFBP-1 to -6, and ALS.

| Assay Parameter | ELISA-1 | ELISA-2 |
| --- | --- | --- |
| Detection limit, AU/mL | 0.12 | 1.13 |
| Standard range, AU/mL | 0.78–50 | 3.13–50 |
| Intrassay CV, % | 3.5–6.6 | 4.3–7.6 |
| Interassay CV, % | 4.8–9.7 | 5.3–10.6 |
| Recovery of added complex, % | 84 + 4.6 | 90 + 9.2 |
| Recovery after dilution, % | 107 + 11.3 | 96 + 12.4 |

Serum IGFBP-3 complexes were analysed in replicate aliquot of samples stored at RT, 4° C. and −20° C. As measured by both ELISA-1 and ELISA-2, IGFBP-3 complexes demonstrated high stability at all temperatures for up to 3 days of storage, and recoveries at 4° C. and −20° C.

were at least 85% of the day 0 values (FIGS. 4A–4C, 5A–5C). Serum-based standards stored and analysed as above demonstrated similar stability, and IGFBP-3 complexes in a pool of fresh sera stored at −20° C. demonstrated at least 2 months stability.

Despite the complexity of their design, the ELISA-1 and ELISA-2 assays for IGFBP complex demonstrated acceptable analytical performance characteristics. The finding of relatively high stability of the IGFBP-3 complexes at various temperature and even in diluted form was unexpected and was instrumental in the success of the development of the assays. The demonstrated linearity of the assays in response to sample dilution may suggest measurement of only the tightly bound IGFBP-3 ternary complexes. Antibody binding and sample dilution may induce IGF dissociation and, thus removal of loosely bound complexes.

B. COMPARISON WITH PRIOR ART ASSAYS

Plasma samples from subjects with untreated GHRD (n=11) and age-matched normal subjects (n=16), and serum samples from adults with acromegaly (n=8) or GHD (n=5) were simultaneously analysed by ELISA-1 and ELISA-2 and for IGF-I, IGF-II, IGFBP-3 and total ALS levels.

Regression analysis of data showed high degree of correlations between IGFBP-3 complex ELISA-1 and -2 versus IGFs, IGFBP-3 and total ALS levels (Table 7, and FIGS. 6A–9B). The best overall correlations were observed in comparisons with IGF-I levels, while correlation against IGF-II levels were relatively poor. The flattened "low-end" appearance of correlation graphs are due to significant differences in the relative levels of the various analytes as a function of age (FIG. 10) as well as clinical conditions, and not necessarily due to poor low end correlations. In fact, correlations in the GHRD range was the same as those involving all sample values.

TABLE 7

Correlation matrix for IGFBP-3 complex ELISA comparison with ALS, IGF-I, IGF-II and IGFBP-3 - X, comparative ELISA methods. Y, ELISA-1, IGFBP-3/IGF-I; ELISA-2, IGFBP-3/ALS.

| X | Y | Slope | intercept | R2 | p |
|---|---|---|---|---|---|
| IGF-1 | ELISA-1 | 1.03 | 25.2 | 0.92 | <0.005 |
|  | ELISA-2 | 0.39 | 11.3 | 0.96 | <0.005 |
| IGF-II | ELISA-1 | 245 | 1.63 | 0.32 | 0.124 |
|  | ELISA-2 | 104 | 0.66 | 0.37 | 0.066 |
| IGFPB-3 | ELISA-1 | 173 | 194 | 0.84 | <0.005 |
|  | ELISA-2 | 64.9 | 68.1 | 0.84 | <0.005 |
| ALS | ELISA-1 | 19.35 | 152 | 0.87 | <0.005 |
|  | ELISA-2 | 49.6 | 7.1 | 0.84 | <0.005 |

Although the number of normal samples in various age groups were small, the overall pattern of IGFs, IGFBP-3 and ALS levels versus age were similar to those previously reported, with levels showing significant rise during pubertal age (21, 34, 35). As expected, IGFBP-3 complex levels were similarly affected by age. However, IGF-I based complexes measured by ELISA-1 showed the widest variations, being lowest in the youngest and oldest age groups and highest during pubertal age (FIG. 10).

In plots of mean analyte levels as a percentage of the corresponding mean of normal values, the mean of IGFBP-3 complex levels measured in GHRD and GHD subjects by ELISA-1 were less than 8% and 2% of the mean of normal values, respectively. The next largest differences were observed for IGF-I levels; the mean IGF-I levels in GHRD and GHD subjects were less than 13% and less than 24% of the mean of normal values (FIG. 11). In comparative distribution plots of the individual values, IGFBP-3 complex levels by ELISA-1 demonstrated similar if not better discrimination between the various sample groups, particularly between GHRD, normals and GHD subjects (FIGS. 12A–12E).

In several experiments involving randomly selected samples, the IGFBP complex ELISAs showed significant correlation with IGF-I, IGFBP-3 and ALS levels. This was subsequently confirmed by the preliminary clinical evaluations involving samples from subjects with GHRD, their age-matched normal controls, and specimens from acromegalic and GHD adults. Overall, both ELISA-I and ELISA-2 demonstrated high correlation with IGF-I, IGFBP-3 and ALS levels. This supports the reported observations that most of circulating IGFs and IGFBP-3 are primarily present in the ternary protein complex and that IGF availability may be a key determinant of ternary complex formation (4–12).

Of interest was the observation that the IGFBP complexes measured by ELISA-1 showed the widest relative variations as a function of age. The IGFBP complex levels of the individual samples were lowest in the younger age group and highest in the older, pubertal range subjects (FIG. 10). Similarly, in comparative distribution plots of the individual sample values, ELISA-1 demonstrated a similar, if not better discrimination between the various sample groups (FIGS. 13A–13E). The relatively lower IGFBP complex measured in younger age group by ELISA-1 may suggest availability of proportionally higher amount of IGF-I in the free (or dissociable) form in this age group, as has been recently reported for early infancy (48).

C. CONCLUSIONS

The data presented here establish that the antibodies described herein can be selected on the basis of their epitope maps and employed in a successful capture-detection ELISA assay format. Additional antibody mapping can be performed in the manner described here. In particular, it would be beneficial to identify anti-IGFBP antibodies whose binding is unaffected by IGF-I or ALS binding. Such antibodies would allow the assay of total IGFBP-3 without regard for the degree of complex formation.

In addition to the two antibody pairs exemplified above (ELISA-1 and -2), other antibody pairs or even triplets can be optimized in a manner similar to that described herein. Hence, the above examples are not to be construed as limiting, but rather as illustrative of the many antibody combinations that can be employed in a capture-detection format.

References (the following articles are incorporated herein by reference):

1. Rotwein P (1991) Structure, evolution, expression and regulation of insulin-like growth factors I and II [review]. *Growth Factors* 5:3–18.
2. Daughaday W H, Rotwein P (1989) Insulin-like growth factors I and II. Peptide, messenger ribonucleic acid and gene structures, serum and tissue concentration [review]. *Endocrin. Rev.* 10:68–91.
3. LeRoith D, et al (1991) Insulin-like growth factors and their receptors as growth regulators in normal physiology and pathological states [review]. *Trends Endocrinol. Metabol.* 2:134–139.
4. Jones J I, Clemmons D R (1995) Insulin-like growth factors and their binding proteins: Biological Actions [review]. *Endocrin Rev.* 16:3–34.
5. Rosenfeld R G, et al. (1990) Insulin-like growth factor-binding proteins [review]. *Recent Prog. Horm. Res.* 46:99–163.
6. Shimasaki S, Ling N (1991) Identification and molecular characterization of insulin-like growth factor binding proteins (IGFBP-1, -2, -3, 4, -5 and 6) [review]. *Prog. Growth Factor Res.* 1:243–266.
7. Lamson G, et al. (1991) Insulin-like growth factor binding proteins: Structural and molecular relationships [review]. *Growth Factors* 5:19–28.
8. Holly J M P, Martin J I (1994) IGFBPs: A review of methodological aspects of their purification, analysis and regulation [review]. *Growth Regul.* 4(supp. 1):20–30.
9. Cohen P, Rosenfeld R G (1994) Physiologic and clinical relevance of the insulin-like growth factor binding proteins [review]. *Curr. Opin. Pediatr.* 6:462–467.
10. Baxter R C, Martin J I. (1989) Structure of the Mr 140,000 growth factor binding protein complex: determination by reconstitution and affinity labelling. *Proc. Natl. Acad. Sci. USA*. 86:6898–6902.
11. Baxter R C (1988) Characterization of the acid-labile subunit of the growth hormone dependent insulin-like growth factor binding protein complex. *Clin. Endocrinol. Metab.* 67:265–272.
12. Baxter R C, et al. (1989) High molecular weight insulin-like growth factor binding protein complex. Purification properties of the acid-labile subunit from human serum. *J. Biol. Chem.* 264:11843–11848.
13. Baxter R C (1990) Circulating levels and molecular distribution of the acid-labile subunit of the high molecular weight insulin-ike growth factor binding protein complex. *J. Clin. Endocrinol. Metab.* 70:1347–1353.
14. Martin J L, Baxter R C (1992) Insulin growth factor binding protein-3: biochemistry and physiology. *Growth Regul.* 2:88–99.
15. Khosravi M J, et al. (1997) Acid-labile subunit of human insulin-like growth factor binding protein complex: Measurement, molecular and clinical evaluation. *J. Clin. Endocrinol. Metab.* 82:3944–3951.
16. Giudice L C (1995) Editorial: IGF Binding protein-3 protease regulation: How sweet it is *J. Clin. Endrocrinol Metabol.* 80:2279–2281.
17. Rajah R, et al. Insulin-like growth factor binding protein (IGFBP) proteases: functional regulators of cell growth. *Prog. Growth Factor Res.* 6:273–284, 1995.
18. Jones J L et al. (1991) Phosphorylation of insulin-like growth factor (IGF)-binding protein 1 in cell culture and in vivo: effects on affinity for IGF-I. *Proc. Natl. Acad. Sci. USA* 88:7481–7485.
19. Khosravi M J, et al. (1997) Immunoassay of insulin-like growth factor binding protein-1. *Clin. Chem.* 43:523–532.
20. Lee P D K, et al. (1990) Efficacy of insulin-like growth factor I levels in predicting the response to provocative growth hormone testing. *Pediatr. Res.* 27:45–51.
21. Rosenfeld R G, et al. (1995) Diagnostic controversy: The diagnosis of childhood growth hormone deficiency revisited. *J. Clin. Endocrinol. Metab.* 80:1532–1540.
22. Rosenfeld R G (1997) Editorial: Is growth hormone deficiency a viable diagnosis. *J. Clin. Endocrinol. Metab.* 82:349–351.
23. Tillmann V, et al. (1997) Biochemical tests in the diagnosis of childhood growth hormone deficiency. *J. Clin. Endocrinol. Metab.* 82:531–535.
24. Attanasio A F, et al. (1997) Adult growth hormone (GH)-deficient patients demonstrate heterogeneity between childhood onset and adult onset before and during human GH treatment. *J. Clin. Endocrinol. Metab.* 82:82–88.
25. Thoren M, et al. (1997) Serum insulin-like growth factor I (IGF-I), IGF-binding protein-1 and -3 and the acid-labile subunit as serum markers of body composition during growth hormone (GH) therapy in adults with GH deficiency. *J. Clin. Endocrinol. Metab.* 82:223–228.
26. Lee P D K, Rosenfeld R G (1987) Clinical utility of insulin-like growth factor assays [review]. *Pediatrician* 14:154–61.
27. Powell D R, et al. (1986) Serum somatomedin levels in adults with chronic renal failure: the importance of measuring insulin-like growth factor-I (IGF-I) and IGF-II in acid-chromatographed uremic serum. *J. Clin. Endocrinol. Metab.* 63:1186–92.
28. Daughaday W H, et al. (1980) Inhibition of access of bound somatomedin to membrane receptor and immunobinding sites: A comparison of radioreceptor and radioimmunoassay of somatomedin in native and acid-ethanol-extracted serum. *J. Clin. Endocrinol. Metab.* 51:781–8.
29. Blum W F, et al. (1988) A specific radioimmunoassay for insulin-like growth factor II: the interference of IGF binding proteins can be blocked by excess IGF-I. *Acta Endocrinol. (Copenh)* 118:374–80.
30. Bang P, et al. (1991) Comparison of acid-ethanol extraction, and acid-gel filtration prior to IGF-I and IGF-II radioimmunoassays: improvement of determinations in acid-ethanol extracts by the use of tncated IGF-I as radioligand. *Acta Endocrinol. (Copenh)* 124:620–29.
31. Mesiano S, et al. (1988) Failure of acid-ethanol treatment to prevent interference by binding proteins in radioligand assays for insulin-like growth factors. *J. Endocrinol.* 119:453–60.
32. Breier B H, et al. (1991) Radioimmunoassay for insulin-like growth factor-I: solutions to some potential problems and pitfalls. *J. Endocrinol.* 128:347–57.
33. Mohan S, Baylink D (1995) Development of a simple valid method for the complete removal of insulin-like growth factor (IGF)-binding proteins from IGFs in human serum and other biological fluids: comparison with acid-ethanol treatment and $C_{18}$Sep-Pak separation. *J. Clin. Endocrinol. Metab.* 80:637–47.
34. Juul A, et al. (1994) Serum insulin-like growth factor-1 in 1030 healthy children, adolescents and adults; relation to age, sex, stage of puberty, testicular size and body mass index. *J. Clin. Endocrinol. Metab.* 78:744–752.
35. Juul A, et al. (1995) Serum levels of insulin-like growth factor (IGF) binding protein-3 in healthy infants, children and adolescents: the relation to IGF-I, IGF-II, IGFBP-1, IGFBP-2, age, sex, body mass index and pubertal maturation. *J. Clin. Endocrinol. Metab.* 80:2534–2542.
36. Deboer H et al. (1996) Monitoring of growth hormone replacement therapy in adults based on measurement of serum markers. *J. Clin. Endocrinol. Metab.* 79:872–876.
37. Khosravi M J, et al. (1996) A non-competitive ELISA for human serum insulin-like growth factor-I. *Clin. Chem.* 42:1147–1154.
38. Khosravi M J, et al. (1996) Development of a non-competitive immunoenzymometric assay for human insulin-like growth factor-II in serum. 10*th Intl Cong. Endocrinol.* San Francisco, Calif. p3–551.
39. Diamandi A, et al. (1995) A non-competitive immunoenzymatic assay for insulin-like growth factor binding protein-3 in serum. Proc. 77*th Meeting of the Endocrine Soc.*, Washington DC P2–328.
40. Khosravi M J, Morton R C (1991) Novel application of streptavidin-hapten derivative as protein-tracer conjugate in competitive-type immunoassays involving biotinylated detection probes. *Clin. Chem.* 37:58–63.
41. Khosravi M J, et al. (1995) ultrasensitive immunoassay for prostate-specific antigen based on conventional colorimetric detection. *Clin. Biochem.* 28:407–414.
42. Khosravi M J, Diamandis E P (1987) Immunofluorometry of choriogonadotropin by time-resolved fluorescence 43. Lee P K D, et al. (1996) Active insulin-like growth factor-I (IGF-I) assays. Webster: DSL Technical Publication.
44. Vorwerk P, et al. (1997) Synthesis of IGFBP-3 fragments in baculovirus system and characterization of monoclonal anti-IGFBP-3 antibodies. *J. Clin. Endocrinol. Metab.* 82:2368–2370.
45. Booth B A, et al. (1996) IGFBP-3 proteolysis by plasmin, thrombin, serum: heparin binding, IGF binding, and structure of fragments. *Am. J. Physiol.* 271:E465–E470.
46. Manes S, et al. (1997) Functional epitope mapping of insulin-like growth factor I (IGF-1) by anti-IGF monoclonal antibodies. *Endocrinol.* 138:905–915.
47. Barreca A, et al. (1995) Effect of the acid-labile subunit on the binding of insulin-like growth factor (IGF)-binding protein-3 to [$^{125}$I]IGF-I. *J. Clin. Endocrinol. Metab.* 80:1318–1324.
48. Hasegawa Y, et al. (1997) High ratio of free to total insulin-like growth factor-I in early infancy. *J. Clin. Endocrinol. Metab.* 82:156–158.
49. Harlow E, et al. (1988) ANTIBODIES. New York, Cold Spring Harbor Laboratory.
50. Liu F, et al. (1994) *J. Clin. Endocrinol. Metab.* 79:1883–1886.

What is claimed is:

1. A kit for an assay of a native ternary complex of IGFBP-3 and IGF and ALS or a native binary complex of IGFBP-3 and ALS or IGF, said kit comprising a capture-antibody and a detection-antibody, wherein said antibodies do not bind to overlapping epitopes and do not effect dissociation of a native ternary complex of IGFBP-3 and IGF and ALS or a native binary complex of IGFBP-3 and ALS or IGF (collectively called the IGFBP-complex), and wherein one of said antibodies binds to IGFBP-3 in the IGFBP-complex and the other of said antibodies binds to IGF or ALS in the IGFBP-complex, thus allowing specific detection of the IGFBP-complex.

2. The kit of claim 1, wherein said capture-antibody is bound to a solid support and said detection-antibody is coupled with a label.

3. The kit of claim 1, wherein the capture-antibody is an anti-IGFBP-3 antibody that binds to an epitope in a N-termiinal region or to an epitope in an intermediate sequence of IGFBP-3 and the detection-antibody is an anti-IGF or an anti-ALS antibody.

4. The kit of claim 1, wherein the capture-antibody is an anti-IGFBP-3 antibody which binds to an epitope in an N-terminal region of IGFBP-3 and the detection-antibody is an anti-IGF-I antibody which binds to an epitope in a C-terminal region of IGF-I.

5. The kit of claim 4, wherein said antibodies are monoclonal antibodies.

6. The kit of claim 1, wherein the capture-antibody is an anti-IGFBP-3 antibody which binds to an epitope in an intermediate sequence of IGFBP-3 and the detection-antibody is an anti-ALS antibody that binds to an epitope in a N-terminal region of ALS.

7. The kit of claim 6, wherein said antibodies are monoclonal antibodies.

8. The kit of any of claims 2–7, further comprising a label detection means, a binding buffer, a wash buffer, a detection buffer and a control standard.

9. A method of detecting an amount of a native ternary complex of IGFBP-3 and IGF and ALS or a native binary complex of IGFBP-3 and ALS or IGF in a body fluid, said method comprising:

a. contacting a solid phase coupled to an anti-IGFBP-3 antibody with a body fluid to specifically capture a native ternary complex of IGFBP-3 and IGF and ALS or a native binary complex of IGFBP-3 and ALS or IGF (collectively called the IGFBP-complex);

b. washing the solid phase with a first wash buffer;

c. contacting the solid phase with an anti-IGF-I or anti-ALS antibody coupled to a label to specifically bind to the captured IGFBP-complex;

d. washing the solid phase with a second wash buffer; and e. detecting said label remaining with said solid phase after said washing step wherein an amount of label detected in step (e) correlates with the amount of the native ternary or binary complex in said body fluid.

10. The method of claim 9, wherein the label is horseradish peroxidase or biotin.

11. The method of claim 9, wherein the anti-IGFBP-3 antibody binds to an epitope in a N-terminal region of IGFBP-3 and the anti-IGF-I antibody binds to an epitope in C-terminal region of IGF-I; or the anti-IGFBP-3 antibody binds to an epitope in an intermediate sequence of IGFBP-3 and the anti-ALS antibody binds to an epitope in a N-terminal region of ALS.

12. The method of claim 11, wherein the label is horseradish peroxidase or biotin and the solid phase is a microtitre well plate.

13. The method of claim 11, wherein said antibodies are monoclonal antibodies.

14. A method of monitoring hormone replacement therapy, said method comprising collection of a body fluid from an individual undergoing hormone replacement therapy and testing said body fluid with the method of claim 9 wherein the amount of the native ternary or binary complex in the body fluid monitors effects of the therapy in the individual.

15. The method of claim 14, wherein the body fluid is collected from a human, bovine, porcine, equine, canine, feline, or ovine individual.

16. A method of detecting an amount of a native ternary complex of IGFBP-3 and IGF and ALS or a native binary complex of IGFBP-3 and ALS or IGF in a body fluid, said method comprising:

a. contacting a solid phase coupled to an anti-IGFBP-3 antibody, which binds to an epitope in a N-terminal region of IGFBP-3 or an intermediate sequence of IGFBP-3, with a body fluid to specifically capture a native ternary complex of IGFBP-3 and IGF and ALS or a native binary complex of IGFBP-3 and ALS or IGF (collectively called the IGFBP-complex);

b. washing the solid phase with a first wash buffer;

c. contacting the solid phase with an anti-IGF-I or anti-ALS antibody, which binds to an epitope in a C-terminal region of IGF-I or a N-terminal region of ALS, respectively, coupled to a label to specifically bind to the captured IGFBP-complex;

d. washing the solid phase with a second wash buffer; and e. detecting said label remaining with said solid phase after said washing step wherein an amount of label detected in step (e) correlates with the amount of the native ternary or binary complex in said body fluid.

17. A method of determining a growth hormone status of an individual with a growth-related disease or a susceptibility to a growth-related disease, comprising:

a. collecting a body fluid of said individual;

b. contacting a solid phase coupled to an anti-IGFBP-3 monoclonal antibody with said body fluid to specifically capture a native ternary complex of IGFBP-3 and IGF and ALS or a native binary complex of IGFBP-3 and ALS or IGF (IGFBP-complex);

c. contacting said solid phase with an anti-IGF-I or anti-ALS monoclonal antibody coupled to a label to specifically bind to and detect the captured IGFBP-complex; and d. detecting said label, wherein an amount of label detected correlates with the growth hormone status of said individual.

18. The method of claim 17, wherein said growth-related disease is selected from the group consisting of hypoglycaemia, diabetes, deficient nutritional states, breast cancer, prostate cancer, immune deficiencies, fetal growth retardation, gigantism, acromegaly, hyperpituitarism, pituitary dwarfism, GH deficiency, GH excess, GH receptor defect, thyomegalia and Alzheimer.

19. The method of claim 17, wherein the individual is human, bovine, porcine, equine, canine, feline, or ovine.

20. A method of monitoring a treatment of an individual with a growth-related disease or susceptibility to a growth-related disease, comprising:

a. contacting a solid phase coupled to an anti-IGFBP-3 antibody with a body fluid of an individual having or susceptible to a growth-related disease to specifically capture a native ternary complex of IGF and IGFBP-3 and ALS or a native binary complex of IGF and ALS or IGF (IGFBP-complex);

b. contacting said captured IGFBP complex with an anti-IGF-I or anti-ALS antibody coupled to a label to specifically bind to and detect the IGFBP-complex; and c. detecting said label, wherein an amount of label detected correlates with said individual's response to a treatment.

21. The method of claim 20, wherein said growth-related disease is selected from the group consisting of hypoglycaemia, diabetes, deficient nutritional states, breast cancer, prostate cancer, immune deficiencies, fetal growth retardation, gigantism, acromegaly, hyperpituitarism, pituitary dwarfism, GH deficiency, GH excess, GH receptor defect, thyomegalia and Alzheimer.

22. The method of claim 17 or 20, wherein the anti-IGFBP-3 antibody binds to an epitope in a N-terminal region of IGFBP-3 and the anti-IGF-I antibody binds to an epitope in a C-terminal region of IGF-I; or the anti-IGFBP-3 antibody binds to an epitope in an intermediate sequence of IGFBP-3 and the anti-ALS antibody binds to an epitope in a N-terminal region of ALS.

* * * * *